US012678024B2

(12) United States Patent
Ariyasu et al.

(10) Patent No.: US 12,678,024 B2
(45) Date of Patent: Jul. 14, 2026

(54) PROCESSING DEVICE, PROCESSING PROGRAM, PROCESSING METHOD, AND PROCESSING SYSTEM

(71) Applicant: AILLIS INC., Tokyo (JP)

(72) Inventors: Yuji Ariyasu, Tokyo (JP); Masashi Sode, Tokyo (JP); Wataru Takahashi, Tokyo (JP); Yoshihiro Todoroki, Tokyo (JP); Atsushi Fukuda, Tokyo (JP); Hiroshi Yoshihara, Tokyo (JP)

(73) Assignee: AILLIS INC. (JP)

( * ) Notice: Subject to any disclaimer, the term of this patent is extended or adjusted under 35 U.S.C. 154(b) by 105 days.

(21) Appl. No.: 18/404,970

(22) Filed: Jan. 5, 2024

(65) Prior Publication Data

US 2024/0130604 A1     Apr. 25, 2024

Related U.S. Application Data

(63) Continuation of application No. PCT/JP2021/026442, filed on Jul. 14, 2021.

(51) Int. Cl.
A61B 1/00          (2006.01)
A61B 1/05          (2006.01)
                (Continued)

(52) U.S. Cl.
CPC .......... A61B 1/000096 (2022.02); A61B 1/05 (2013.01); A61B 1/24 (2013.01); G16H 50/20 (2018.01); A61B 1/04 (2013.01)

(58) Field of Classification Search
CPC ..... A61B 1/000096; A61B 1/24; G16H 50/20
See application file for complete search history.

(56) References Cited

U.S. PATENT DOCUMENTS

2018/0353073 A1    12/2018   Boucher et al.
2019/0087959 A1     3/2019   Kitamura et al.
                (Continued)

FOREIGN PATENT DOCUMENTS

JP       2018-527997 A     9/2018
WO       2017-199408 A1    11/2017
                (Continued)

OTHER PUBLICATIONS

"Aillis Inc. applied for approval of the world's first AI-equipped medical device for infectious disease diagnosis that can dedect influenza"; https://prtimes.jp/main/html/rd/p/000000014.000035813. html; published on-line Jun. 16, 2021 (total 4 pages) (English abstract provided on p. 1).
                (Continued)

*Primary Examiner* — Colin T. Sakamoto
(74) *Attorney, Agent, or Firm* — Harness, Dickey & Pierce, P.L.C.

(57)          ABSTRACT

A processing device is provided for processing an image obtained by imaging the inside of the oral cavity for use in diagnosis of the inside of the oral cavity. The processing device includes at least one processor. The at least one processor performs processing for acquiring one or more determination images of a subject through a camera for capturing an image of the subject including at least a part of a user's oral cavity, determining a possibility of contracting a predetermined disease based on a trained determination model stored in a memory to determine the possibility of contracting the predetermined disease and the one or more acquired determination images, and outputting information indicating the determined possibility of contracting the predetermined disease.

12 Claims, 18 Drawing Sheets

(51) Int. Cl.
*A61B 1/24* (2006.01)
*G16H 50/20* (2018.01)
*A61B 1/04* (2006.01)

(56) References Cited

U.S. PATENT DOCUMENTS

| | | | |
|---|---|---|---|
| 2019/0268538 A1 | 8/2019 | Shiratani | |
| 2021/0059534 A1* | 3/2021 | Okiyama | ................. A61B 1/32 |

FOREIGN PATENT DOCUMENTS

| | | |
|---|---|---|
| WO | 2018-105062 A1 | 6/2018 |
| WO | 2019-131327 A1 | 7/2019 |

OTHER PUBLICATIONS

Akihiko Miyamoto et al. "Posterior Pharyngeal Wall Follicles as a Diagnostic Marker of Influenza During Physical Excamination: Considering Their Meaning and Value"; Journal of Nippon Medical School; Year 2013; pp. 11-18 (total 8 pages) (English explanation provided on p. 1).

Tae Keun Yoo, et al. "Toward automated severe pharyngitis detection with smartphone camera using deep learning networks"; Computers in Biology and Medicine; vol. 125; Aug. 20, 2020; pp. 1-9 (total 9 pages).

Sho Okiyama, et al. "Examining the Use of an Artificial Intelligence Model to Diagnose Influenza: Development and Validation Study"; Journal of Medical Internet Research; vol. 24; Dec. 23, 2022; pp. 1-13 (total 13 pages).

Hiroshi Yoshihara, et al. "Detection of hypertension from pharyngeal images using deep learning algorithm in primary care settings in Japan"; BMJ Health & Care Informatics; Oct. 23, 2024; pp. 1-9 (total 9 pages).

European Search Report issued in the corresponding European Patent Application No. 21950140.0; dated Mar. 21, 2025 (total 14 pages).

* cited by examiner

| USER ID | SUBJECT IMAGE | CANDIDATE | DETERMINAT ION IMAGE | ... |
|---|---|---|---|---|
| U1 | I1 | N1 | S1 | ... |
| U2 | I2 | N2 | S2 | ... |
| U3 | I3 | N3 | S3 | ... |
| U4 | I4 | N4 | S4 | ... |
| U5 | I5 | N5 | S5 | ... |
| ... | ... | ... | ... | ... |

Fig. 7B

| USER ID | ATTRIBUTE | MEDICAL INTERVIEW | TWO-DIMENSI ONAL CODE | DETERMINA TION RESULT | ... |
|---|---|---|---|---|---|
| U1 | A1 | C1 | Q1 | R1 | ... |
| U2 | A2 | C2 | Q2 | R2 | ... |
| U3 | A3 | C3 | Q3 | R3 | ... |
| U4 | A4 | C4 | Q4 | R4 | ... |
| U5 | A5 | C5 | Q1 | R5 | ... |
| ... | ... | ... | ... | ... | ... |

PROCESSING DEVICE, PROCESSING PROGRAM, PROCESSING METHOD, AND PROCESSING SYSTEM

CROSS-REFERENCE TO RELATED APPLICATIONS

The present application is a continuation application of International Application No. PCT/JP2021/026442, filed on Jul. 14, 2021, which is expressly incorporated herein by reference in its entirety.

BACKGROUND

Technical Field

The present disclosure relates to a processing device, a processing program, a processing method, and a processing system for processing an image of a subject captured by a camera.

Related Art

Conventionally, it has been known that a doctor diagnoses, for example, a viral cold by observing a change in the condition of the user's oral cavity. Non Patent Literature 1 (Miyamoto and Watanabe, "Consideration of Meanings and Values of Examination Findings of Pharynx (Influenza Follicles)", Journal of the Japan Medical Journal 72 (1): 11 to 18 (2013)) reports that lymphoid follicles appearing in the deepest part of the pharynx located in the oral cavity have a pattern unique to influenza. Lymphoid follicles having this unique pattern are called influenza follicles, are a characteristic sign of influenza, and appear about two hours after the onset of symptoms. However, such a pharynx region has been diagnosed by doctor's direct visual inspection, and diagnosis using images has not been made.

SUMMARY

Therefore, in view of the above-described technology, it is an object of the present disclosure to provide a processing device, a processing program, a processing method, or a processing system for determining the possibility of contracting a predetermined disease using a subject determination image obtained by imaging the oral cavity of a user according to various embodiments.

According to one aspect of the present disclosure, there is provided "a processing device including at least one processor, wherein the at least one processor performs processing for acquiring one or more determination images of a subject through a camera for capturing an image of the subject including at least a part of a user's oral cavity, determining a possibility of contracting a predetermined disease based on a trained determination model stored in a memory to determine the possibility of contracting the predetermined disease and the one or more acquired determination images, and outputting information indicating the determined possibility of contracting the predetermined disease".

According to one aspect of the present disclosure, there is provided "a processing program executed by at least one processor to cause the at least one processor to function to acquire one or more determination images of a subject through a camera for capturing an image of the subject including at least a part of a user's oral cavity, determine a possibility of contracting a predetermined disease based on a trained determination model stored in a memory to determine the possibility of contracting the predetermined disease and the one or more acquired determination images, and output information indicating the determined possibility of contracting the predetermined disease".

According to one aspect of the present disclosure, there is provided "a processing method executed by at least one processor, the method including a step of acquiring one or more determination images of a subject through a camera for capturing an image of the subject including at least a part of a user's oral cavity, a step of determining a possibility of contracting a predetermined disease based on a trained determination model stored in a memory to determine the possibility of contracting the predetermined disease and the one or more acquired determination images, and a step of outputting information indicating the determined possibility of contracting the predetermined disease".

According to one aspect of the present disclosure, there is provided "a processing system including an imaging device including a camera for capturing an image of a subject including at least a part of the user's oral cavity and the above-described processing device connected to the imaging device through a wired or wireless network".

Advantageous Effects of the Invention

According to the present disclosure, it is possible to provide a processing device, a processing program, a processing method, and a processing system suitable for processing an image obtained by imaging the inside of the oral cavity for use in diagnosis of the inside of the oral cavity.

Note that, the above effects are merely exemplary for convenience of description, and are not restrictive. In addition to or instead of the above effect, any effect described in the present disclosure or an effect obvious to those skilled in the art can also be achieved.

BRIEF DESCRIPTION OF THE DRAWINGS

FIG. 7A is a diagram conceptually illustrating an image management table stored in a processing device 100 according to an embodiment of the present disclosure.

FIG. 7B is a diagram conceptually illustrating a user table stored in the processing device 100 according to an embodiment of the present disclosure.

DETAILED DESCRIPTION

Figure 1:
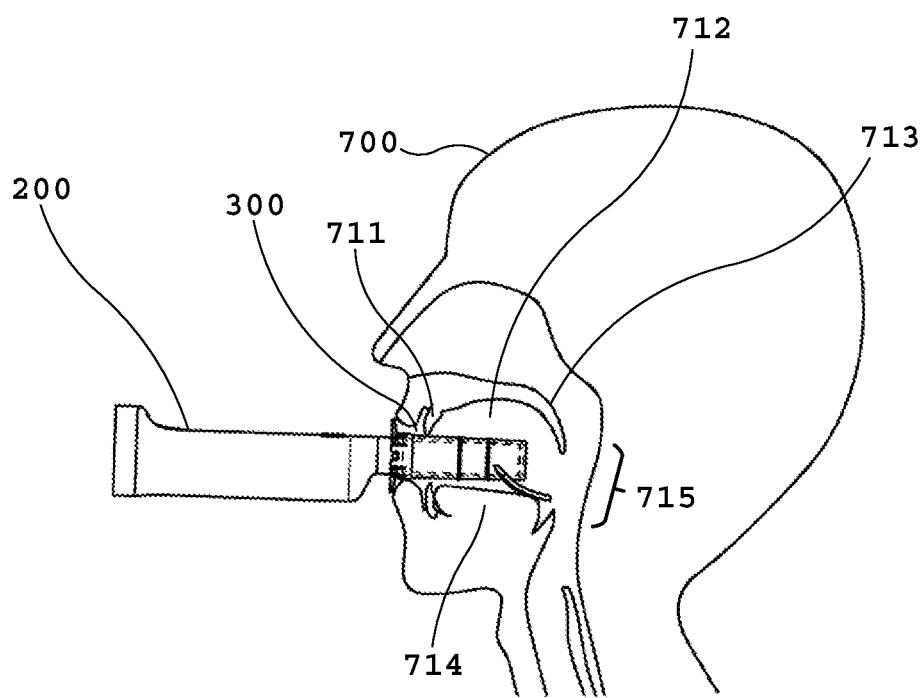
FIG. 1 is a diagram illustrating a use state of a processing system 1 according to an embodiment of the present disclosure.

Various embodiments of the present disclosure will be described with reference to the accompanying diagrams. Note that, common components in the diagrams are denoted by the same reference numerals.

First Embodiment

1. Overview of Processing System 1

A processing system 1 according to the present disclosure is mainly used for imaging the inside of a user's oral cavity to obtain a subject image. In particular, the processing system 1 is used to image the back of the throat of the oral cavity, specifically, the pharynx. Therefore, in the following description, a case where the processing system 1 according to the present disclosure is used for imaging the pharynx will be mainly described. However, the pharynx is an example of a site to be imaged, and as a matter of course, the processing system 1 according to the present disclosure can be suitably used even for other sites such as tonsils in the oral cavity.

The processing system 1 according to the present disclosure is used to determine the possibility of contracting a predetermined disease from a subject image obtained by imaging a subject including at least the pharynx region of the user's oral cavity and to diagnose the predetermined disease or assist the diagnosis for the predetermined disease. An example of the disease determined by the processing system 1 is influenza. The possibility of contracting influenza is usually diagnosed by examining the user's pharynx or tonsils or by determining the presence or absence of findings such as follicles in the pharynx region. However, it is possible to perform diagnosis or assistance by determining the possibility of contracting influenza using the processing system 1 and outputting the result. Note that, the determination of the possibility of contracting influenza is one example. The processing system 1 can be suitably used for any disease that causes a difference in findings in the oral cavity depending on the disease. Note that, the difference in findings is not limited to those found by a doctor or the like and whose existence is medically known. For example, a difference that can be recognized by a person other than a doctor or a difference that can be detected by artificial intelligence or an image recognition technology can be suitably applied to the processing system 1. Examples of such diseases include, in addition to influenza, streptococcus infection, adenovirus infection, EB virus infection, mycoplasma infection, infections such as hand-foot and mouth disease, herpangina, and candidiasis, diseases exhibiting vascular disorders or mucosal disorders such as arteriosclerosis, diabetes, and hypertension, and tumors such as tongue cancer and pharyngeal cancer.

Note that, in the present disclosure, terms such as "determination" and "diagnosis" for a disease are used, but these do not necessarily mean a definite determination or diagnosis by a doctor. For example, the processing system 1 of the present disclosure may be used by the user himself or herself or by an operator other than a doctor, and the determination or diagnosis may be performed by a processing device 100 included in the processing system 1.

In the present disclosure, users to be imaged by an imaging device 200 can include any human being, such as a patient, a subject, a diagnostic user, and a healthy person. In the present disclosure, the operator who holds the imaging device 200 and performs an imaging operation is not limited to medical personnel such as doctors, nurses, and laboratory technicians, but may include any person such as the user himself or herself. The processing system 1 according to the present disclosure is typically assumed to be used in a medical institution. However, the present invention is not limited to this case, and the place of use may be any place such as the user's home, school, or workplace.

In the present disclosure, as described above, the subject only needs to include at least a part of the oral cavity of the user. The disease to be determined may be any disease as long as a difference appears in findings in the oral cavity. However, in the following description, a case will be described in which the subject includes the pharynx or the vicinity of the pharynx and the possibility of contracting influenza is determined as a disease.

In the present disclosure, the subject image or the determination image may be one or more moving images or one or more still images. As an example of the operation, when a power button is pressed, a through image is captured by the camera, and the captured through image is displayed on a display 203. Thereafter, when the operator presses an imaging button, one or more still images are captured by the camera, and the captured images are displayed on the display 203. Alternatively, when the user presses an imaging button, the capturing of a moving image is started, and an image captured by the camera during that time is displayed on the display 203. Then, when the imaging button is pressed again, the capturing of the moving image is ended. As described above, in a series of operations, various images such as a through image, a still image, and a moving image are captured by the camera and displayed on the display. However, the subject image does not mean only a specific image among these images, but may include all of the images captured by the camera.

FIG. 1 is a diagram illustrating a use state of the processing system 1 according to an embodiment of the present disclosure. According to FIG. 1, the processing system 1 according to the present disclosure includes the processing device 100 and the imaging device 200. The operator attaches an auxiliary tool 300 to the distal end of the imaging device 200 so as to cover the distal end, and inserts the imaging device 200 into the user's oral cavity 710 together with the auxiliary tool 300. Specifically, first, the operator (who may be a user 700 or may be different from the user 700) attaches the auxiliary tool 300 to the distal end of the imaging device 200 so as to cover the distal end. Then, the operator inserts the imaging device 200 to which the auxiliary tool 300 is attached into the oral cavity 710. At this time, the distal end of the auxiliary tool 300 passes through incisors 711 and is inserted to the vicinity of the soft palate 713. That is, the imaging device 200 is similarly inserted up to the vicinity of the soft palate 713. At this time, the tongue 714 is pushed downward by the auxiliary tool 300 (functions as a tongue depressor) to restrict the movement of the tongue 714. The soft palate 713 is pushed upward by the distal end of the auxiliary tool 300. As a result, the operator can secure a favorable field of view of the imaging device 200 and satisfactorily image the pharynx 715 located in front of the imaging device 200.

The captured subject image (typically, an image including the pharynx 715) is transmitted from the imaging device 200 to the processing device 100 communicably connected by a wired or wireless network. When the processor of the processing device 100 that has received the subject image processes a program stored in the memory, a determination image to be used for determination is selected from the subject image, and the possibility of contracting a predetermined disease is determined. Then, the result is output to a display or the like.

Figure 2:
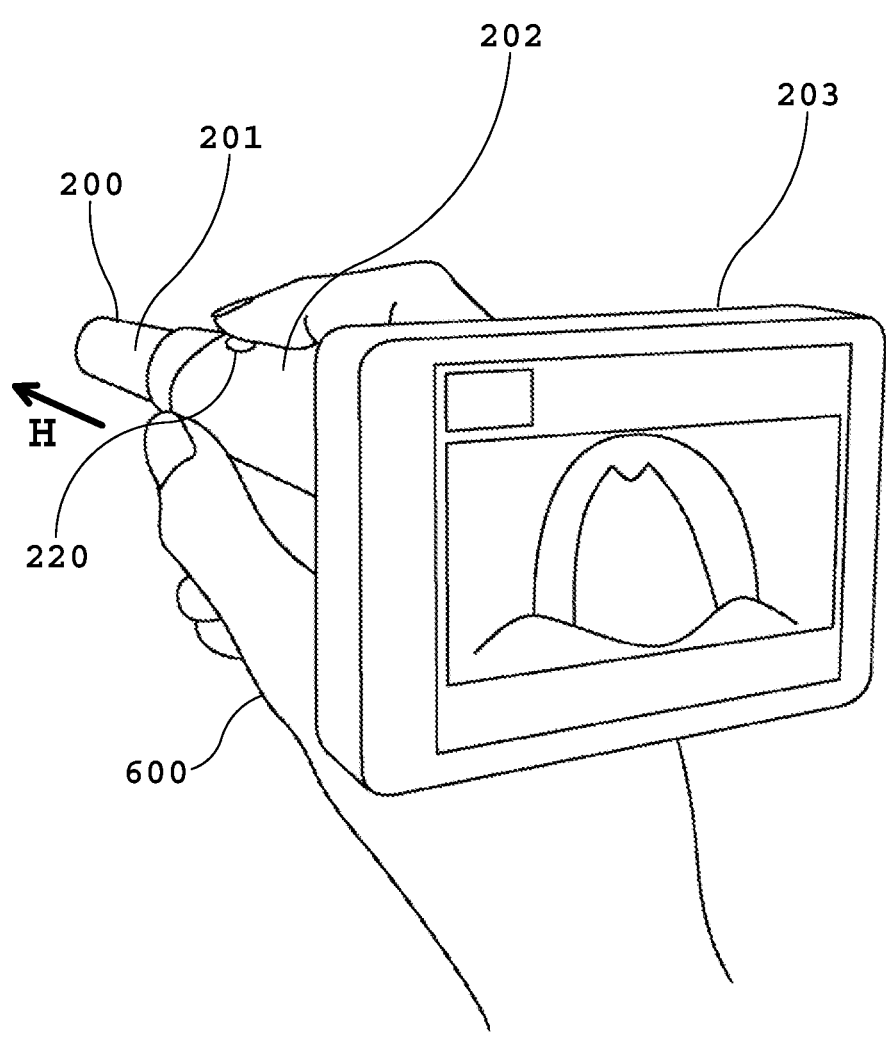
FIG. 2 is a diagram illustrating a use state of the processing system 1 according to an embodiment of the present disclosure.

FIG. 2 is a diagram illustrating a use state of the processing system 1 according to an embodiment of the present disclosure. Specifically, FIG. 2 is a diagram illustrating a state in which the imaging device 200 of the processing system 1 is held by an operator 600. According to FIG. 2, the imaging device 200 includes a main body 201, a grip 202, and a display 203 from the side inserted into the oral cavity. The main body 201 and the grip 202 are formed in an approximately columnar shape having a predetermined length along an insertion direction H into the oral cavity. The display 203 is disposed on a side of the grip 202 not facing the main body 201. Therefore, the imaging device 200 is formed in an approximately columnar shape as a whole, and is held by the operator 600 in a manner similar to holding a pencil. That is, since the display panel of the display 203 faces the direction of the operator 600 himself or herself in the use state, it is possible to easily handle the imaging device 200 while checking the subject image captured by the imaging device 200 in real time.

When the operator 600 holds the grip 202 in a direction in which the subject image is displayed in the normal direction on the display 203, an imaging button 220 is arranged on the top surface side of the grip. Therefore, when the operator 600 holds the grip 202, the operator 600 can easily press the imaging button 220 with his or her index finger or the like.

2. Configuration of Processing System 1

Figure 3:
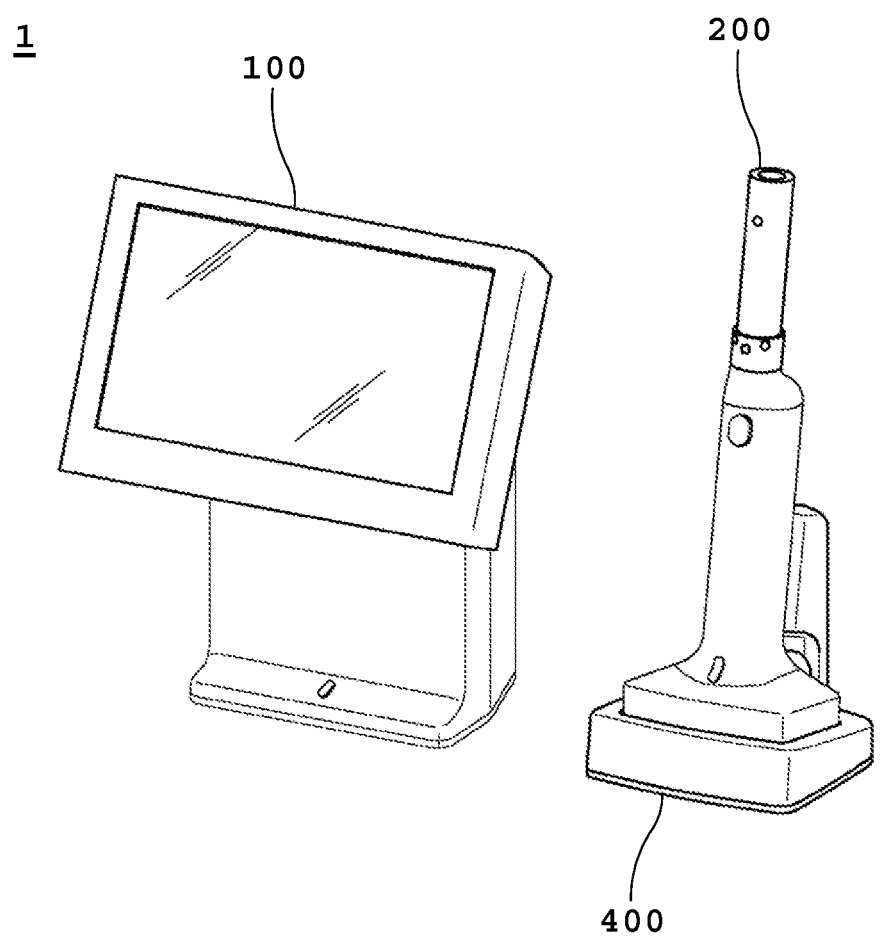
FIG. 3 is a schematic diagram of the processing system 1 according to an embodiment of the present disclosure.

FIG. 3 is a schematic diagram of the processing system 1 according to an embodiment of the present disclosure.

According to FIG. 3, the processing system 1 includes the processing device 100 and the imaging device 200 communicably connected to the processing device 100 through a wired or wireless network. The processing device 100 receives an operation input by an operator and controls imaging by the imaging device 200. The processing device 100 processes the subject image captured by the imaging device 200 to determine a possibility that the user will contract influenza. The processing device 100 outputs the determined result and notifies the user, the operator, the doctor, and the like of the result.

The distal end of the imaging device 200 is inserted into the oral cavity of the user to image the inside of the oral cavity, particularly the pharynx. The specific imaging processing will be described later. The captured subject image is transmitted to the processing device 100 through a wired or wireless network.

Note that, the processing system 1 can further include a mounting table 400 as necessary. The imaging device 200 can be stably mounted on the mounting table 400. The mounting table 400 is connected to a power source through a wired cable, so that power can be supplied from the power supply terminal of the mounting table 400 to the imaging device 200 through the power supply port of the imaging device 200.

Figure 4:
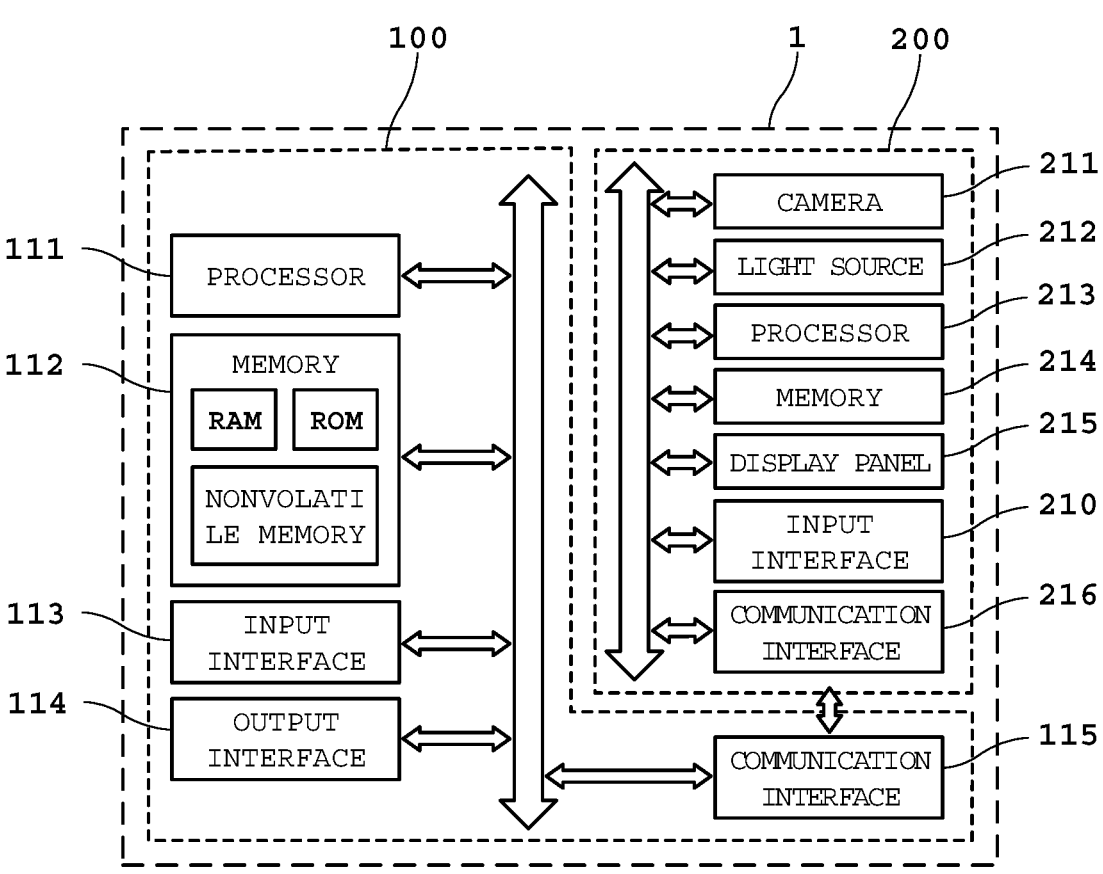
FIG. 4 is a block diagram illustrating the configuration of the processing system 1 according to an embodiment of the present disclosure.

FIG. 4 is a block diagram illustrating the configuration of the processing system 1 according to an embodiment of the present disclosure. According to FIG. 4, the processing system 1 includes the processing device 100 including a processor 111, a memory 112, an input interface 113, an output interface 114, and a communication interface 115 and the imaging device 200 including a camera 211, a light source 212, a processor 213, a memory 214, a display panel 215, an input interface 210, and a communication interface 216. These components are electrically connected to each other through a control line and a data line. Note that, the processing system 1 does not need to include all of the components illustrated in FIG. 4, and some of the components can be omitted or other components can be added. For example, the processing system 1 can include a battery for driving each component.

First, in the processing device 100, the processor 111 functions as a control unit that controls other components of the processing system 1 based on a program stored in the memory 112. Based on the program stored in the memory 112, the processor 111 controls driving of the camera 211 and driving of the light source 212, and stores the subject image received from the imaging device 200 in the memory 112 and processes the stored subject image. Specifically, based on the program stored in the memory 112, the processor 111 executes a process of acquiring a subject image of a subject from the camera 211, a process of acquiring candidates for a determination image by inputting the acquired subject image to the determination image selection model, a process of acquiring a determination image from the acquired candidates for the determination image based on the similarity between the images, a process of acquiring at least one of the medical interview information and the attribute information of the user, a process of determining the possibility of contracting influenza based on the trained determination model stored in the memory 112, one or more acquired determination images, and at least one of the medical interview information and the attribute information of the user as necessary, a process of outputting information indicating the possibility of contracting a predetermined disease that is determined to diagnose the morbidity of the predetermined disease or assist the diagnosis, and the like.

The processor 111 is mainly configured by one or more CPUs, but a GPU, an FPGA, and the like may be appropriately combined.

The memory 112 includes a RAM, a ROM, a nonvolatile memory, an HDD, and the like, and functions as a storage unit. The memory 112 stores instruction commands for various controls of the processing system 1 according to the present embodiment as programs. Specifically, the memory 112 stores programs to be executed by the processor 111, such as a process of acquiring a subject image of a subject from the camera 211, a process of acquiring candidates for a determination image by inputting the acquired subject image to the determination image selection model, a process of acquiring a determination image from the acquired candidates for the determination image based on the similarity between the images, a process of acquiring at least one of the medical interview information and the attribute information of the user, a process of determining the possibility of contracting influenza based on the trained determination model stored in the memory 112, one or more acquired determination images, and at least one of the medical interview information and the attribute information of the user as necessary, and a process of outputting information indicating the possibility of contracting a predetermined disease that is determined to diagnose the morbidity of the predetermined disease or assist the diagnosis. In addition to the programs, the memory 112 stores an image management table for managing a subject image captured by the camera 211 of the imaging device 200, the image, and the like, a user table for storing attribute information, medical interview information, determination results, and the like of the user, and the like. The memory 112 stores trained models, such as a trained determination image selection model used for selecting a determination image from a subject image and a trained determination model for determining the possibility of contracting a disease from a determination image.

The input interface 113 functions as an input unit that receives the operator's instruction input to the processing device 100 and the imaging device 200. Examples of the input interface 113 include physical key buttons such as an "imaging button" for giving an instruction to start/end recording by the imaging device 200, a "confirmation button" for performing various selections, a "return/cancel button" for returning to the previous screen or canceling an input confirmation operation, a cross key button for moving a pointer or the like output to the output interface 114, an on/off key for turning on/off the power of the processing device 100, and a character input key button for inputting various characters. Note that, as the input interface 113, it is also possible to use a touch panel that is provided so as to be superimposed on a display functioning as the output interface 114 and has an input coordinate system corresponding to the display coordinate system of the display. In this case, an icon corresponding to the physical key is displayed on the display, and the operator performs an instruction input through the touch panel to select each icon. The method of detecting the instruction input of the user using a touch panel may be any method such as a capacitance type or a resistive film type. The input interface 113 does not always need to be physically provided in the processing device 100, and may be connected as necessary through a wired or wireless network.

The output interface 114 functions as an output unit for outputting a subject image captured by the imaging device 200 or outputting a result determined by the processor 111. Examples of the output interface 114 include a display including a liquid crystal panel, an organic EL display, a plasma display, or the like. However, the processing device 100 itself does not necessarily need to include a display. For example, an interface for connecting to a display or the like connectable to the processing device 100 through a wired or wireless network can also function as the output interface 114 that outputs display data to the display or the like.

The communication interface 115 functions as a communication unit for transmitting and receiving various commands related to start of imaging and image data captured by the imaging device 200 to and from the imaging device 200 connected through a wired or wireless network. Examples of the communication interface 115 include various devices such as a connector for wired communication such as USB and SCSI, a transmission/reception device for wireless communication such as wireless LAN, Bluetooth (registered trademark), and infrared rays, and various connection terminals for a printed mounting board and a flexible mounting board.

Next, in the imaging device 200, the camera 211 functions as an imaging unit that detects reflected light reflected on the oral cavity, which is a subject, and generates a subject image. The camera 211 includes, as an example, a CMOS image sensor, a lens system for enabling a desired function, and a drive system in order to detect the light. The image sensor is not limited to the CMOS image sensor, and other sensors such as a CCD image sensor can be used. Although not particularly illustrated, the camera 211 can have an autofocus function, and is preferably set, for example, such that the focus is located at a specific portion on the front surface of the lens. The camera 211 can have a zoom function, and is preferably set to capture an image at an appropriate magnification according to the size of the pharynx or the influenza follicle.

It is known that lymphoid follicles appearing in the deepest part of the pharynx located in the oral cavity have a pattern unique to influenza. Lymphoid follicles having this unique pattern are called influenza follicles, are a characteristic sign of influenza, and appear about two hours after the onset of symptoms. As described above, the processing system 1 of the present embodiment is used to determine the user's possibility of contracting influenza, for example, by imaging the pharynx of the oral cavity and detecting the follicles. For this reason, when the imaging device 200 is inserted into the oral cavity, the distance between the camera 211 and the subject becomes relatively short. Therefore, the camera 211 preferably has an angle of view ($2\theta$) at which a value calculated by [(distance from the distal end of the camera 211 to the pharyngeal rear wall)*tan $\theta$] is 20 mm or more in the vertical direction and 40 mm or more in the horizontal direction. By using a camera having such an angle of view, even if the camera 211 and the subject are close to each other, imaging of a wider range becomes possible. That is, as the camera 211, a normal camera can be used, but a camera called a wide-angle camera or an ultra-wide-angle camera can also be used.

In the present embodiment, a main subject imaged by the camera 211 is an influenza follicle formed in the pharynx or a pharynx portion. Since the pharynx is generally formed deep in the depth direction, if the depth of field is shallow, the focus is shifted between the anterior part of the pharynx and the posterior part of the pharynx, and it becomes difficult to obtain a subject image suitable for use in determination in the processing device 100. Therefore, the camera 211 has a depth of field of at least 20 mm or more, preferably 30 mm or more. By using a camera having such a depth of field, it is possible to obtain a subject image having a focus at any site from the anterior part of the pharynx to the posterior part of the pharynx.

The light source 212 is driven by an instruction from the processing device 100 or the imaging device 200, and functions as a light source unit for irradiating the oral cavity with light. The light source 212 includes one or more light sources. In the present embodiment, the light source 212 includes one or more LEDs, and light having a predetermined frequency band is emitted from each LED in the direction of the oral cavity. As the light source 212, light having a desired band among an ultraviolet light band, a visible light band, and an infrared light band, or a combination thereof is used. Note that, when determining the possibility of contracting influenza in the processing device 100, it is preferable to use light in a short wavelength band of an ultraviolet light band.

The processor 213 functions as a control unit that controls other components of the imaging device 200 based on the program stored in the memory 214. Based on the program stored in the memory 214, the processor 213 controls the driving of the camera 211 and the drawing of the light source 212, and also controls the storage of the subject image captured by the camera 211 in the memory 214. The processor 213 controls the output of the subject image and the user information stored in the memory 214 to the display 203 and the transmission thereof to the processing device 100. The processor 213 is mainly configured by one or more CPUs, but may be appropriately combined with other processors.

The memory 214 includes a RAM, a ROM, a nonvolatile memory, an HDD, and the like, and functions as a storage unit. The memory 214 stores, as a program, instruction commands for various controls of the imaging device 200. In addition to the program, the memory 214 stores a subject image captured by the camera 211, various kinds of information of the user, and the like.

The display panel 215 is provided on the display 203 and functions as a display unit for displaying the subject image captured by the imaging device 200. The display panel 215 is configured by a liquid crystal panel, but is not limited to the liquid crystal panel, and may be configured by an organic EL display, a plasma display, or the like.

The input interface 210 functions as an input unit that receives the user's instruction input to the processing device 100 and the imaging device 200. Examples of the input interface 210 include physical key buttons such as an "imaging button" for giving an instruction to start/end recording by the imaging device 200, a "power button" for turning on/off the power of the imaging device 200, a "confirmation button" for performing various selections, a "return/cancel button" for returning to the previous screen or canceling an input confirmation operation, and a cross key button for moving an icon or the like displayed on the display panel 215. Note that, these various buttons and keys may be physically prepared, or may be selectable using a touch panel or the like displayed as an icon on the display panel 215 and arranged as the input interface 210 in a superimposed manner on the display panel 215. The method of detecting the instruction input of the user using a touch panel may be any method such as a capacitance type or a resistive film type.

The communication interface 216 functions as a communication unit for transmitting and receiving information to and from the imaging device 200 and/or other devices. Examples of the communication interface 216 include various devices such as a connector for wired communication such as USB and SCSI, a transmission/reception device for wireless communication such as wireless LAN, Bluetooth (registered trademark), and infrared rays, and various connection terminals for a printed mounting board and a flexible mounting board.

Figure 5:
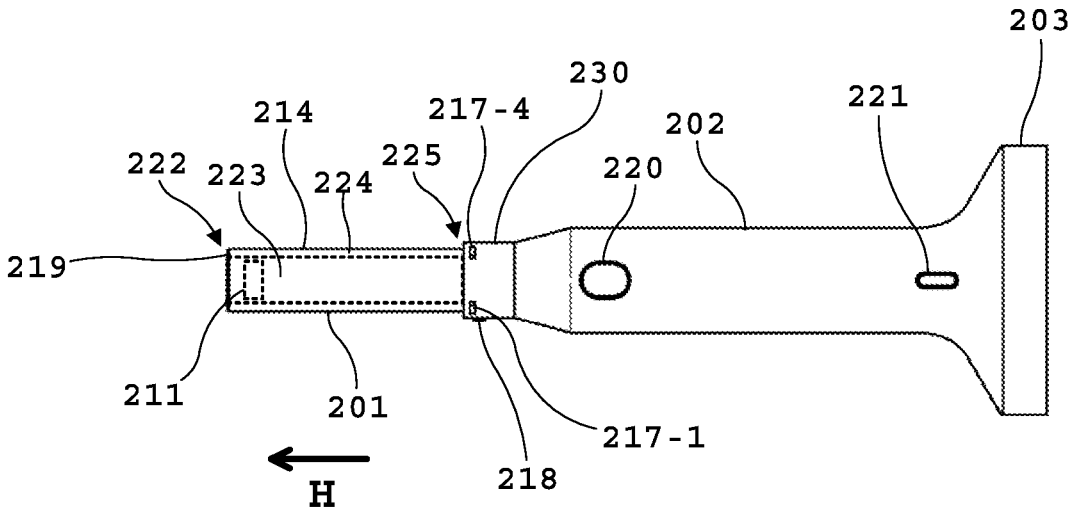
FIG. 5 is a schematic diagram illustrating the configuration of an upper surface of an imaging device 200 according to an embodiment of the present disclosure.

FIG. 5 is a top view illustrating the configuration of the imaging device 200 according to an embodiment of the present disclosure. Specifically, FIG. 5 is a diagram illustrating a state in which the imaging device 200 including the main body 201, the grip 202, and the display 203 from the side inserted into the oral cavity is viewed from above. According to FIG. 5, the main body 201 includes a base end 225 and a distal end 222, and is a columnar body having a predetermined length in a direction in which light is emitted from the light source 212, that is, in a direction approximately parallel to the direction H of insertion into the oral cavity. Then, at least the distal end 222 of the main body 201 is inserted into the oral cavity.

The main body 201 is formed in a columnar shape having a hollow cylindrical shape whose cross section is a perfect circle. The wall portion 224 may be formed of any material as long as the material can guide light into the wall portion, and can be obtained by using a thermoplastic resin as an example. As the thermoplastic resin, polyolefin-based resins such as chain polyolefin-based resins (polypropylene-based resins and the like) and cyclic polyolefin-based resins (norbornene-based resins and the like), cellulose ester-based resins such as triacetyl cellulose and diacetyl cellulose, polyester-based resins, polycarbonate-based resins, (meth) acrylic resins, polystyrene-based resins, or mixtures and copolymers thereof are used. That is, the wall portion 224 of the main body 201 functions as a light guide body for guiding the light emitted from the light source in the oral cavity or toward the diffusion plate.

Since the main body 201 is formed in a hollow shape, a housing space 223 is formed on the inner surface by the wall portion 224. The camera 211 is housed in the housing space 223. Note that, the main body 201 only needs to be formed in a columnar shape having the housing space 223. Therefore, the housing space 223 does not need to have a cylindrical shape having a perfect circular cross section, and may have an elliptical or polygonal cross section. The inside of the main body 201 does not necessarily need to be formed hollow.

The distal end of the grip 202 is connected to the base end 225 of the main body 201. The user holds the grip 202 to perform operations such as inserting and removing the imaging device 200. The grip 202 is formed by a columnar body having a predetermined length in a direction approximately parallel to the direction H of insertion into the oral cavity, that is, along the longitudinal direction of main body 201, and is disposed on the same straight line as the main body 201 in the direction H. Note that, in the present embodiment, the cross section in the vertical direction is formed to be approximately oval, but the cross section is not necessarily oval, and may be a perfect circle, an ellipse, or a polygon.

The grip 202 has a connecting portion 230 formed at a position closest to the base end 225 of the main body 201, so that the grip 202 is connected to the main body 201 through the connecting portion 230. An engagement protrusion 217 (217-1 to 217-4) for positioning the auxiliary tool 300 and a positioning protrusion 218 are provided on the outer periphery of the connecting portion 230. The engagement protrusion 217 engages with an engagement protrusion 318 (318-1 to 318-4) provided on the auxiliary tool 300. The positioning protrusion 218 is inserted into an insertion hole 321 provided in the auxiliary tool 300 to position the imaging device 200 and the auxiliary tool 300 relative to each other. Note that, in the present embodiment, in the engagement protrusion 217 of the main body 201, a total of four engagement protrusions (engagement protrusions 217-1 to 217-4) are arranged at equal intervals on the surface of the grip 202 so as to be located near the base end 225 of the main body 201. One positioning protrusion 218 is disposed between the engagement protrusions 217 on the surface of the grip 202 so as to be located near the base end 225 of the main body 201. However, the present invention is not limited thereto, and only one of the engagement protrusion 217 and the positioning protrusion 218 may be disposed. The number of engagement protrusions 217 and the number of positioning protrusions 218 may be any number as long as the number is one or more.

The grip 202 includes the imaging button 220 at a position close to the base end 225 of the main body 201 on its upper surface, that is, near the distal end of the grip 202 in the insertion direction H in the oral cavity. Therefore, when the operator 600 holds the grip 202, the operator 600 can easily press the imaging button 220 with his or her index finger or the like. On the upper surface of the grip 202, the power button 221 is disposed at a position close to the display 203, that is, at a position opposite to the imaging button 220 of the grip 202. Therefore, it is possible to prevent the operator 600 from accidentally pressing the power button 221 while holding the grip 202 to capture an image.

The display 203 has an approximately rectangular parallelepiped shape as a whole, and is disposed on the same straight line as the main body 201 in the direction H. The display 203 includes the display panel 215 on a surface in a direction (that is, a direction toward the user) opposite to the direction H of insertion into the oral cavity. Therefore, the display 203 is formed such that a surface including the display panel is approximately perpendicular to the longitudinal direction of the main body 201 and the grip 202 formed so as to be approximately parallel to the direction H of insertion into the oral cavity. Then, on a surface opposite to the surface including the display panel, the display 203 is connected to the grip 202 on the side of the grip 202 opposite to the oral cavity. Note that, the shape of the display is not limited to the approximately rectangular parallelepiped shape, and may be any shape such as a cylindrical shape.

The diffusion plate 219 is disposed at the distal end 222 of the main body 201, and diffuses light emitted from the light source 212 and passing through the main body 201 toward the inside of the oral cavity. The diffusion plate 219 has a shape corresponding to the cross-sectional shape of a portion of the main body 201 configured to be able to guide light. In the present embodiment, the main body 201 is formed in a hollow cylindrical shape. Therefore, the cross section of the diffusion plate is also formed in a hollow shape corresponding to the shape of the diffusion plate 219.

The camera 211 is used to generate a subject image by detecting reflected light diffused from the diffusion plate 219, emitted into the oral cavity, and reflected on the subject. The camera 211 is disposed on the same straight line as the main body 201 in the direction H on the inner surface of the wall portion 224 of the main body 201, that is, in the housing space 223 formed inside the main body 201. Note that, although only one camera 211 is described in the present embodiment, the imaging device 200 may include a plurality of cameras. By generating subject images using a plurality of cameras, the subject images include information regarding a three-dimensional shape. In the present embodiment, the camera 211 is arranged in the housing space 223 of the main body 201, but may be arranged at the distal end 222 of the main body 201 or in the main body 201 (may be inside the main body 201 or on the outer periphery of the main body 201).

Figure 6:
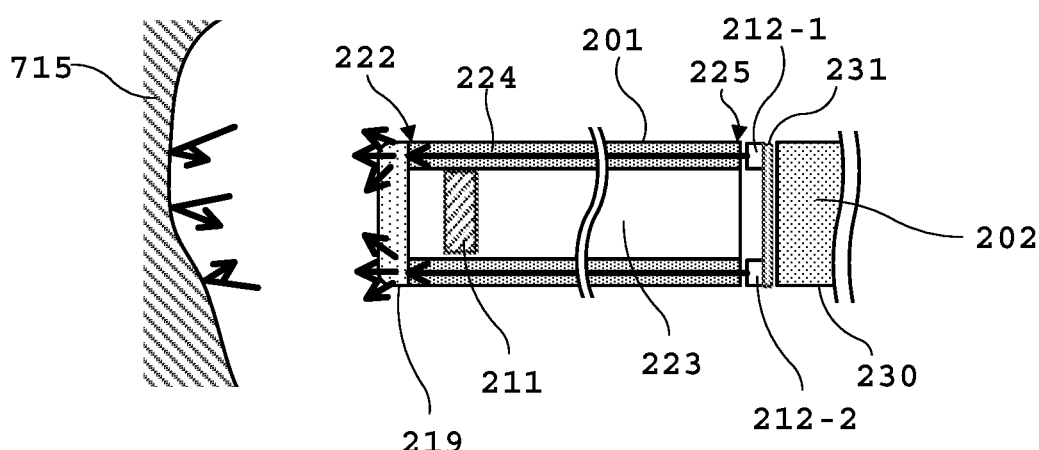
FIG. 6 is a schematic diagram illustrating the cross-sectional configuration of the imaging device 200 according to an embodiment of the present disclosure.

FIG. 6 is a schematic diagram illustrating the cross-sectional configuration of the imaging device 200 according to an embodiment of the present disclosure. According to FIG. 6, in the light source 212, a total of four light sources 212-1 to 212-4 are arranged on the substrate 231 disposed on the distal end side of the grip 202. As an example, each of the light sources 212 includes an LED, and light having a predetermined frequency band is emitted from each LED toward the oral cavity. Specifically, the light emitted from the light source 212 enters the base end 225 of the main body 201, and is guided toward the diffusion plate 219 by the wall portion 224 of the main body 201. The light reaching the diffusion plate 219 is diffused into the oral cavity by the diffusion plate 219. Then, the light diffused by the diffusion plate 219 is reflected to the pharynx 715 or the like that is a subject. When the reflected light reaches the camera 211, a subject image is generated.

Note that, the light sources 212-1 to 212-4 may be configured to be independently controlled. For example, by making some of the light sources 212-1 to 212-4 emit light, it is possible to include a shade of a subject (influenza follicle or the like) having a three-dimensional shape in the subject image. As a result, the subject image includes information on the three-dimensional shape of the subject, the subject can be more clearly determined, and the possibility of contracting influenza can be more accurately determined by the determination algorithm.

In the present embodiment, the light sources 212-1 to 212-4 are arranged on the base end 225 side of the main body 201, but may be arranged at the distal end 222 of the main body 201 or in the main body 201 (may be inside the main body 201 or on the outer periphery of the main body 201).

In the present embodiment, the diffusion plate 219 is used to prevent light emitted from the light source 212 from illuminating only a part of the oral cavity and to generate uniform light. Therefore, as an example, a fine lens array is formed on the surface of the diffusion plate 219, and a lens-shaped diffusion plate having any diffusion angle is used. Instead of this, a diffusion plate that can diffuse light by another method, such as a diffusion plate that achieves a light diffusion function by fine irregularities randomly arranged on the surface, may be used. The diffusion plate 219 may be configured integrally with the main body 201. For example, this can be achieved by forming fine irregularities on the distal end portion of the main body 201.

In the present embodiment, the diffusion plate 219 may be disposed on the distal end 222 side of the main body 201. However, the present invention is not limited thereto, and the diffusion plate 219 may be disposed at any position as long as the position is between the light source 212 and the inside of the oral cavity to which light is to be emitted. For example, the diffusion plate 219 may be arranged at the distal end 222 of the main body 201 or in the main body 201 (may be inside the main body 201 or on the outer periphery of the main body 201).

3. Information Stored in Memory 112 of Processing Device 100

FIG. 7A is a diagram conceptually illustrating an image management table stored in the processing device 100 according to an embodiment of the present disclosure. The information stored in the image management table is updated and stored as needed according to the progress of the processing of the processor 111 of the processing device 100.

According to FIG. 7A, the image management table stores subject image information, candidate information, determination image information, and the like in association with user ID information. The "user ID information" is information for specifying each user with information unique to each user. The user ID information is generated every time a new user is registered by the operator. The "subject image information" is information for specifying a subject image captured by the operator for each user. The subject image is one or more images including a subject captured by the camera of the imaging device 200, and is stored in the memory 112 by being received from the imaging device 200. The "candidate information" is information for specifying an image that is a candidate for selecting a determination image from one or more subject images. The "determination image information" is information for specifying a determination image used for determining the possibility of contracting influenza. Such a determination image is selected from candidate images specified by the candidate information based on the similarity. Note that, as described above, information for specifying each image is stored as the subject image information, the candidate information, and the determination image information. As described above, the information for specifying each image is typically identification information for identifying each image, but may be information indicating the storage location of each image or image data itself of each image.

FIG. 7B is a diagram conceptually illustrating a user table stored in the processing device 100 according to an embodiment of the present disclosure. The information stored in the user table is updated and stored as needed according to the progress of the processing of the processor 111 of the processing device 100.

According to FIG. 7B, attribute information, medical interview information, two-dimensional code information, determination result information, and the like are stored in the user table in association with the user ID information. The "user ID information" is information for specifying each user with information unique to each user. The user ID information is generated every time a new user is registered by the operator. The "attribute information" is, for example, information input by an operator, a user, or the like, and is information related to an individual user such as the name, gender, age, and address of the user. The "medical interview information" is, for example, information input by an operator, a user, or the like, and is information to be used as a reference for diagnosis by a doctor or the like, such as a medical history or a symptom of the user. Examples of such medical interview information include patient background such as body weight, allergy, and basal disease, body temperature, peak body temperature from onset, elapsed time from onset, heart rate, pulse rate, oxygen saturation, blood pressure, medication status, contact status with other influenza patients, joint pain, muscle pain, headache, malaise, loss of appetite, chills, sweating, cough, sore throat, nasal juice/nasal congestion, tonsillitis, digestive symptoms, rash on hands and feet, redness and white of pharynx, swelling of tonsils, history of resection of tonsils, presence or absence of subjective symptoms and physical findings such as strawberry tongue and swelling of anterior cervical lymph node with tenderness, history of influenza vaccination, and vaccination timing. The "two-dimensional code information" is information for specifying a recording medium on which at least one of user ID information, information for specifying the user ID information, attribute information, medical interview information, or a combination thereof is recorded. Such a recording medium does not need to be a two-dimensional code. Instead of the two-dimensional code, various items such as a one-dimensional bar code, multi-dimensional other codes, text information such as specific numbers and characters, and image information can be used. The "determination result information" is information indicating a determination result of the possibility of contracting influenza based on the determination image. An example of such determination result information is a positive rate for influenza. However, the present invention is not limited to the positive rate, and any one indicating the possibility, such as information for specifying positive or negative, may be used. The determination result does not need to be a specific numerical value, and may be in any form such as classification according to the level of the positive rate or classification indicating positive or negative.

Note that, the attribute information or the medical interview information does not need to be input by the user or the operator each time, and may be received from, for example, an electronic medical record device or another terminal device connected through a wired or wireless network. Alternatively, the attribute information or the medical interview information may be acquired by analyzing a subject image captured by the imaging device 200. Although not particularly illustrated in FIGS. 7A and 7B, it is also possible to further store, in the memory 112, information on the current prevalence of infectious diseases that can be used to diagnose influenza or the like or to assist in diagnosis of influenza or the like or information on external factors such as other users' determination results and disease status regarding these infectious diseases.

4. Processing Sequence Executed by Processing Device 100 and Imaging Device 200

Figure 8:
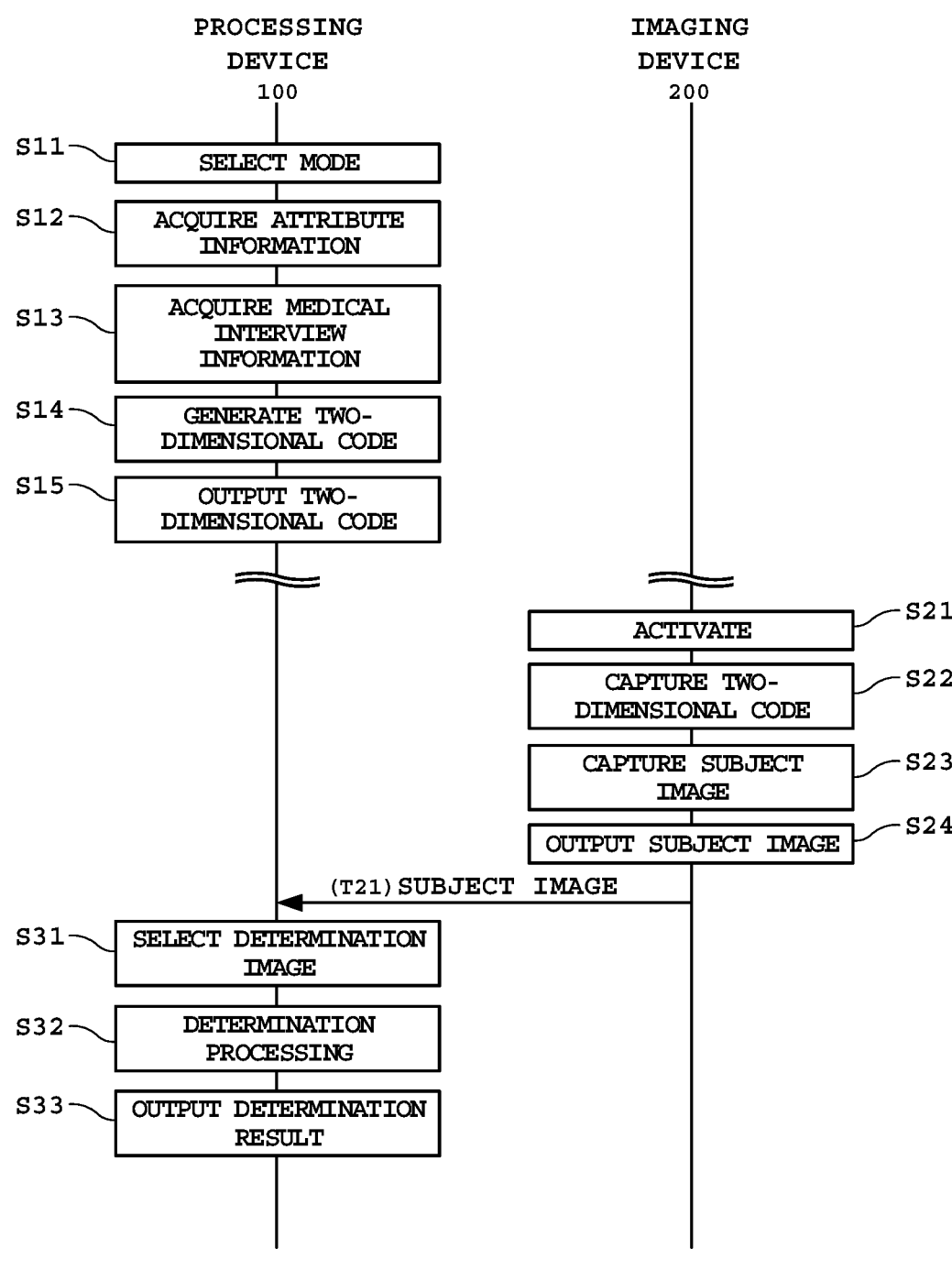
FIG. 8 is a diagram illustrating a processing sequence executed between the processing device 100 and the imaging device 200 according to an embodiment of the present disclosure.

FIG. 8 is a diagram illustrating a processing sequence executed between the processing device 100 and the imaging device 200 according to an embodiment of the present disclosure. Specifically, FIG. 8 illustrates a processing sequence executed after the processing device 100 selects an imaging mode until the imaging device 200 captures a subject image and the processing device 100 outputs a determination result.

According to FIG. 8, the processing device 100 outputs a mode selection screen through the output interface 114, and receives the selection of a mode by the operator through the input interface 113 (S11). Then, when the selection of the imaging mode is received, the processing device 100 outputs an input screen of the attribute information through the output interface 114. The processing device 100 receives an input by the operator or the user through the input interface 113, acquires the attribute information, and stores the attribute information in the user table in association with the user ID information (S12). When the attribute information is acquired, the processing device 100 outputs an input screen of the medical interview information through the output interface 114. The processing device 100 receives an input by the operator or the user through the input interface 113, acquires the medical interview information, and stores the medical interview information in the user table in association with the user ID information (S13). Note that, the acquisition of the attribute information and the medical interview information does not need to be performed at this timing, and can be performed at another timing such as before the determination processing. These pieces of information may be acquired not only by receiving an input through the input interface 113 but also by receiving the information from an electronic medical record device, another terminal device, or the like connected through a wired or wireless network. These pieces of information may be input by an electronic medical record device or another terminal device and then recorded in a recording medium, such as a two-dimensional code, and acquired by imaging the recording medium with a camera or the imaging device 200 connected to the processing device 100. These pieces of information may be acquired by causing a user, an operator, a patient, medical personnel, or the like to fill in a paper medium such as a medical interview sheet, capturing the paper medium with a scanner or the imaging device 200 connected to the processing device 100, and optically performing character recognition.

Under the control of the processor 111, the processing device 100 generates a two-dimensional code in which the user ID information generated in advance is recorded, and stores the two-dimensional code in the memory 112 (S14). Then, the processing device 100 outputs the generated two-dimensional code through the output interface 114 (S15).

Then, the imaging device 200 activates the camera 211 and the like when an input to the input interface 210 (for example, a power button) by the operator is received (S21). Then, the two-dimensional code output through the output interface 114 is captured by the activated camera 211, so that the imaging device 200 reads the user ID information recorded in the two-dimensional code (S22).

Then, the operator covers the distal end of the imaging device 200 with the auxiliary tool 300, and inserts the imaging device 200 into the oral cavity of the user up to a predetermined position. When receiving the input to the input interface 210 (for example, an imaging button) by the operator, the imaging device 200 starts capturing a subject image of the subject including at least a part of the oral cavity (S23). When the capturing of the subject image ends, the imaging device 200 stores the captured subject image in the memory 214 in association with the user ID information read from the two-dimensional code, and outputs the captured subject image to the display panel 215 of the display (S24). Then, when an input from the operator to end the capturing is received through the input interface 210, the imaging device 200 transmits a stored subject image (T21) to the processing device 100 in association with the user ID information through the communication interface 216.

Then, when the subject image is received through the communication interface 115, the processing device 100 stores the subject image in the memory 112 and registers the subject image in the image management table based on the user ID information. The processing device 100 selects a determination image to be used for determining the possibility of contracting influenza from the stored subject images (S31). When the determination image is selected, the processing device 100 performs processing for determining the possibility of contracting influenza using the selected determination image (S32). When the determination result is obtained, the processing device 100 stores the obtained determination result in the user table in association with the user ID information and outputs the determination result through the output interface 114 (S33). As described above, the processing sequence ends.

5. Processing Flow Executed by Processing Device 100 (Mode Selection Processing, Etc.)

Figure 9:
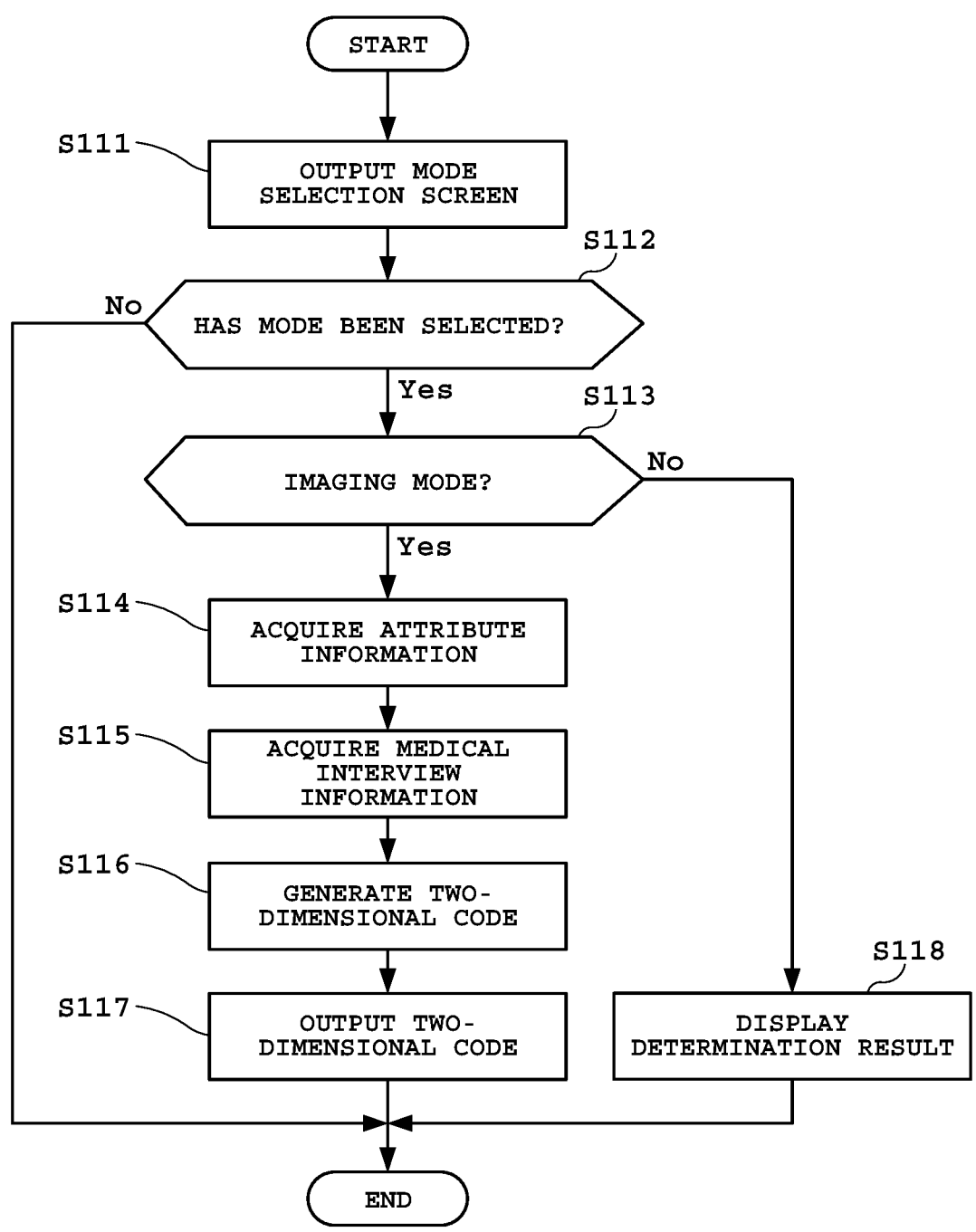
FIG. 9 is a diagram illustrating a processing flow executed in the processing device 100 according to an embodiment of the present disclosure.

FIG. 9 is a diagram illustrating a processing flow executed in the processing device 100 according to an embodiment of the present disclosure. Specifically, FIG. 9 is a diagram illustrating a processing flow executed at a predetermined cycle for the processing according to S11 to S15 in FIG. 8. The processing flow is mainly performed by the processor 111 of the processing device 100 reading and executing a program stored in the memory 112.

Figure 18:
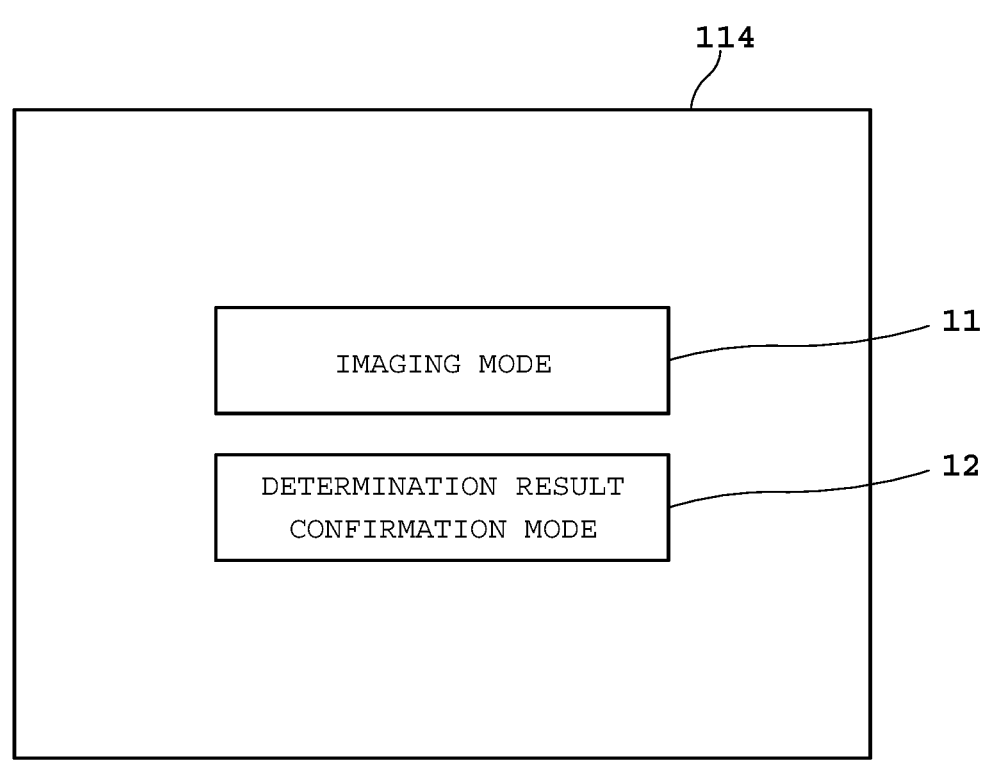
FIG. 18 is a diagram illustrating an example of a screen displayed on the processing device 100 according to an embodiment of the present disclosure.

According to FIG. 9, the processor 111 outputs a mode selection screen through the output interface 114 (S111). Here, FIG. 18 is a diagram illustrating an example of a screen displayed on the processing device 100 according to an embodiment of the present disclosure. Specifically, FIG. 18 illustrates an example of the mode selection screen output in S111 and S112 of FIG. 9. According to FIG. 18, an imaging mode icon 11 for shifting to an imaging mode for capturing a subject image and a determination result confirmation mode icon 12 for shifting to a determination result confirmation mode for outputting, to the display, a result in which the possibility of contracting influenza has already been determined are displayed approximately at the center of the display that functions as the output interface 114. The user can select which mode to shift to by operating the input interface 113.

Returning to FIG. 9 again, the processor 111 determines whether the selection of a mode by the operator has been received through the input interface 113 (S112). At this time, when the processor 111 determines that no input has been made to either the imaging mode icon 11 or the determination result confirmation mode icon 12 illustrated in FIG. 18 and the selection of the mode has not been received, the processing flow ends.

On the other hand, when the processor 111 determines that the mode is selected by receiving the input to either the imaging mode icon 11 or the determination result confirmation mode icon 12 illustrated in FIG. 18, the processor 111 determines whether the imaging mode has been selected (S113). Then, when it is determined that the determination result confirmation mode icon 12 illustrated in FIG. 18 has been selected, the processor 111 displays a desired determination result through the output interface 114 (S118).

On the other hand, when it is determined that the imaging mode icon 11 illustrated in FIG. 18 has been selected, the processor 111 displays a screen for receiving the input of the attribute information of the user on the output interface 114 (not illustrated). The screen includes items such as the name, gender, age, and address of the user, which need to be input as attribute information, and an input box for inputting an answer to each item. Then, the processor 111 acquires information input to each input box through the input interface 113 as attribute information (S114). Then, the processor 111 newly generates user ID information corresponding to the user newly stored in the user table, and stores the attribute information in the user table in association with the user ID information. Note that, when the user ID information is selected in advance before inputting the attribute information, it is possible to omit newly generating the user ID information.

Then, the processor 111 displays, on the output interface 114, a screen for receiving the input of the medical interview information of the user (not illustrated). The screen includes items such as the body temperature, heart rate, medication status, and presence or absence of subjective symptoms of the user, which need to be input as medical interview information, and an input box for inputting an answer to each item. Then, the processor 111 acquires information input to each input box through the input interface 113 as medical interview information, and stores the information in the user table in association with the user ID information (S115).

Note that, the case where the attribute information or the medical interview information is input by the processing device 100 has been described. However, the present invention is not limited thereto, and the information may be acquired by receiving information input to an electronic medical record device or another terminal device connected through a wired or wireless network.

Then, the processor 111 reads user ID information corresponding to the user, including these pieces of information, with reference to the user table, and generates a two-dimensional code in which the user ID information is recorded (S116). The processor 111 stores the generated two-dimensional code in the user table in association with the user ID information, and outputs the two-dimensional code through the output interface 114 (S117). As described above, the processing flow ends.

Figure 19:
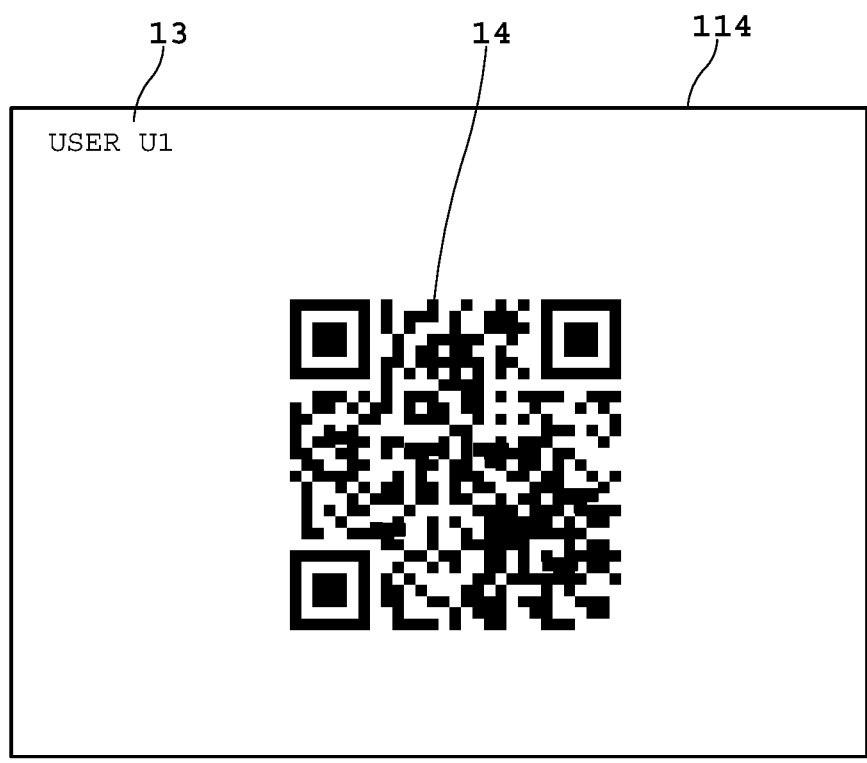
FIG. 19 is a diagram illustrating an example of a screen displayed on the processing device 100 according to an embodiment of the present disclosure.

Here, FIG. 19 is a diagram illustrating an example of a screen displayed on the processing device 100 according to an embodiment of the present disclosure. Specifically, FIG. 19 is a diagram illustrating an example of the display screen of the two-dimensional code output in S117 of FIG. 9. According to FIG. 19, the user ID information of the user, including the attribute information and the like, is displayed in the upper portion of the display functioning as the output interface 114. In addition to this, the two-dimensional code generated in S116 of FIG. 19 is displayed approximately at the center of the display. The user ID information recorded in the two-dimensional code can be read by capturing the two-dimensional code with the imaging device 200.

6. Processing Flow Executed by Imaging Device 200 (Imaging Processing, Etc.)

Figure 10:
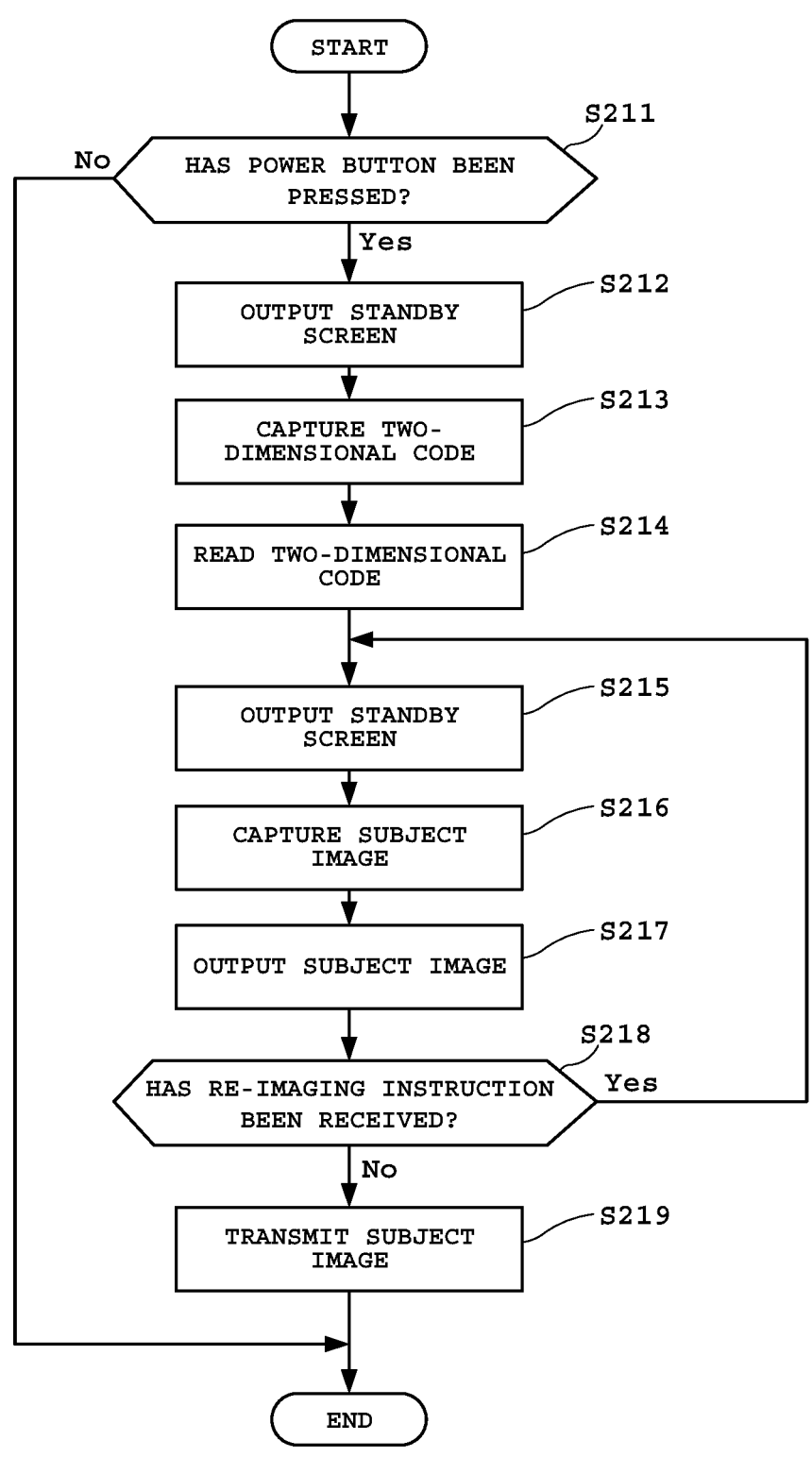
FIG. 10 is a diagram illustrating a processing flow executed in the imaging device 200 according to an embodiment of the present disclosure.

FIG. 10 is a diagram illustrating a processing flow executed in the processing device 100 according to an embodiment of the present disclosure. Specifically, FIG. 10 is a diagram illustrating a processing flow executed at a predetermined cycle for the processing according to S21 to S24 in FIG. 8. The processing flow is mainly performed by the processor 213 of the imaging device 200 reading and executing a program stored in the memory 214.

According to FIG. 10, the processor 213 determines whether an input by the operator has been received through the input interface 210 (for example, a power button) (S211). Note that, at this time, when the processor 213 determines that the input by the operator has not been received, the processing flow ends.

On the other hand, when it is determined that the input by the operator has been received, the processor 213 outputs a standby screen to the display panel 215 (S212). The standby screen (not illustrated) includes a through image captured through the camera 211. Then, when the operator moves the imaging device 200 so that the two-dimensional code output to the output interface 114 of the processing device 100 is included in the angle of view of the camera 211, the processor 213 captures the two-dimensional code with the camera 211 (S213). When the two-dimensional code is captured, the processor 213 reads the user ID information recorded in the two-dimensional code, and stores the read user ID information in the memory 214 (S214). Then, the processor 213 outputs the standby screen to the display panel 215 again (S215).

Then, the operator covers the distal end of the imaging device 200 with the auxiliary tool 300, and inserts the imaging device 200 into the oral cavity of the user up to a predetermined position. Then, when the processor 213 receives an imaging start operation from the operator through the input interface 210 (for example, an imaging button), the processor 213 controls the camera 211 to start capturing the subject image of the subject (S216). The capturing of the subject image is performed by pressing the imaging button to collectively capture a predetermined number of images (for example, 30 images) at predetermined intervals. When the capturing of the subject image ends, the processor 213 stores the captured subject image in the memory 214 in association with the read user ID information. Then, the processor 213 outputs the stored subject image to the display panel 215 (S217).

Here, the operator can take out the imaging device 200 from the oral cavity together with the auxiliary tool 300, check the subject image output to the display panel 215, and input a re-imaging instruction when the desired image is not obtained. Therefore, the processor 213 determines whether an input of a re-imaging instruction by the operator has been received through the input interface 210 (S218). When the input of the re-imaging instruction is received, the processor 213 displays the standby screen in S215 again to enable the capturing of the subject image.

On the other hand, when the input of the re-imaging instruction is not received and the imaging device 200 is returned to the mounting table 400 by the operator and the instruction to end the imaging is received from the processing device 100, the processor 213 transmits the subject image stored in the memory 214 and the user ID information associated with the subject image to the processing device 100 through the communication interface 216 (S219). As described above, the processing flow ends.

7. Processing Flow Executed by Processing Device 100 (Determination Processing, Etc.)

Figure 11:
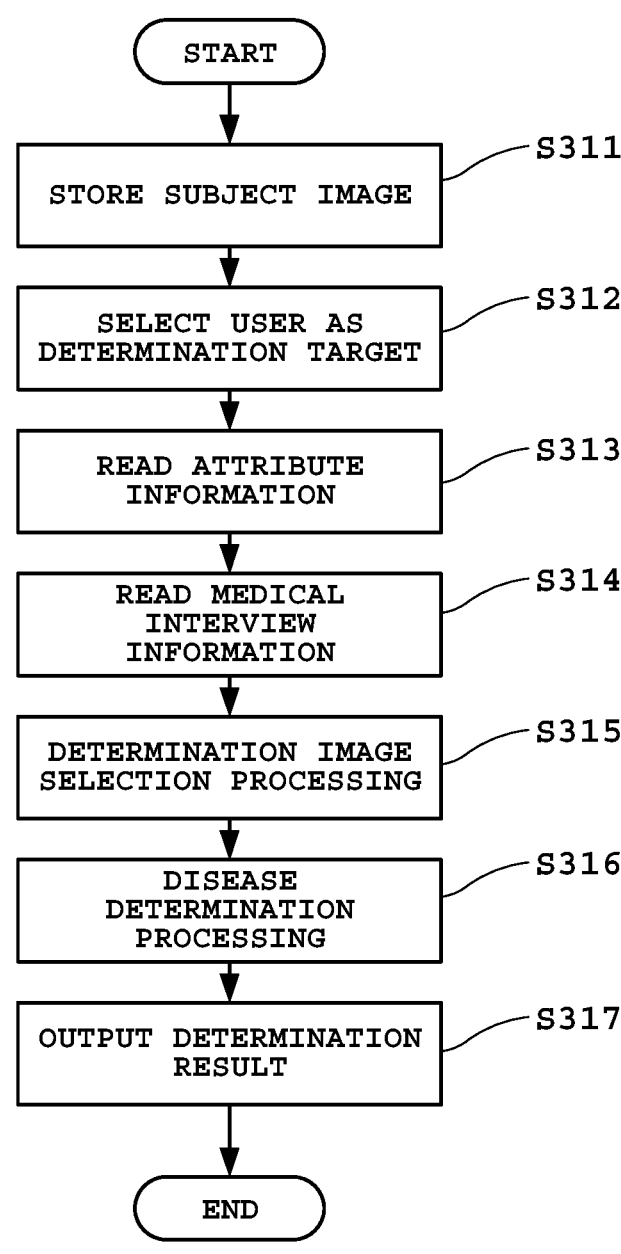
FIG. 11 is a diagram illustrating a processing flow executed in the processing device 100 according to an embodiment of the present disclosure.

FIG. 11 is a diagram illustrating a processing flow executed in the processing device 100 according to an embodiment of the present disclosure. Specifically, FIG. 11 is a diagram illustrating a processing flow executed for the processing according to S31 to S33 in FIG. 8. The processing flow is mainly performed by the processor 111 of the processing device 100 reading and executing a program stored in the memory 112.

According to FIG. 11, when the subject image and the user ID information associated with the subject image are received from the imaging device 200, the processor 111 stores the subject image and the user ID information in the memory 112 and registers the subject image and the user ID information in the image management table (S311). Then, the processor 111 outputs the received user ID information or the attribute information corresponding thereto (for example, the name) through the output interface 114, and receives the selection of the user for whom the possibility of contracting influenza is to be determined (S312). Note that, at this time, when a plurality of pieces of user ID information and a subject image associated with the plurality of pieces of user ID information are received from the imaging device 200, it is possible to output the plurality of pieces of user ID information or attribute information corresponding thereto and select one of the users.

When the selection of the user as a determination target is received through input interface 113, the processor 111 reads the attribute information associated with the user ID information of the user from the user table in the memory 112 (S313). Similarly, the processor 111 reads the medical interview information associated with the user ID information of the user as a determination target from the user table in the memory 112 (S314).

Then, the processor 111 reads the subject image associated with the user ID information of the user selected from the memory 112, and executes processing for the selection of a determination image used to determine the possibility of contracting influenza (S315: details of this selection processing will be described later). Then, the processor 111 executes processing for determining the possibility of contracting influenza based on the selected determination image (S316: details of this determination processing will be described later). When the determination result is obtained by the determination processing, the processor 111 stores the determination result in the user table in association with the user ID information, and outputs the determination result through the output interface 114 (S317). As described above, the processing flow ends.

Figure 12:
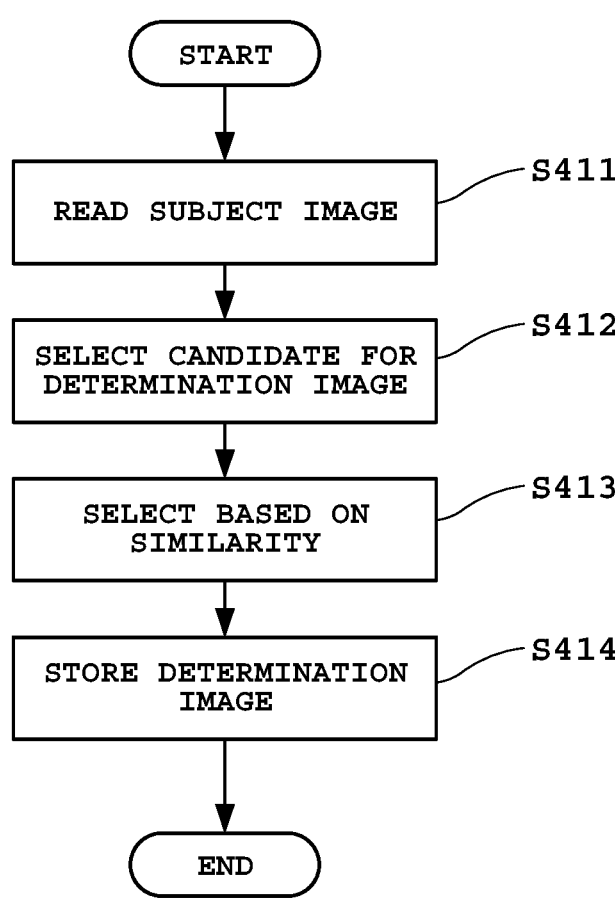
FIG. 12 is a diagram illustrating a processing flow executed in the processing device 100 according to an embodiment of the present disclosure.

FIG. 12 is a diagram illustrating a processing flow executed in the processing device 100 according to an embodiment of the present disclosure. Specifically, FIG. 12 is a diagram illustrating details of the determination image selection processing executed in S315 of FIG. 11. The processing flow is mainly performed by the processor 111 of the processing device 100 reading and executing a program stored in the memory 112.

According to FIG. 12, the processor 111 reads the subject image associated with the user ID information of the user selected from the memory 112 (S411). Then, the processor 412 selects an image that is a candidate for the determination image from the read subject images (S412). As an example, this selection is performed using a trained determination image selection model.

Figure 13:
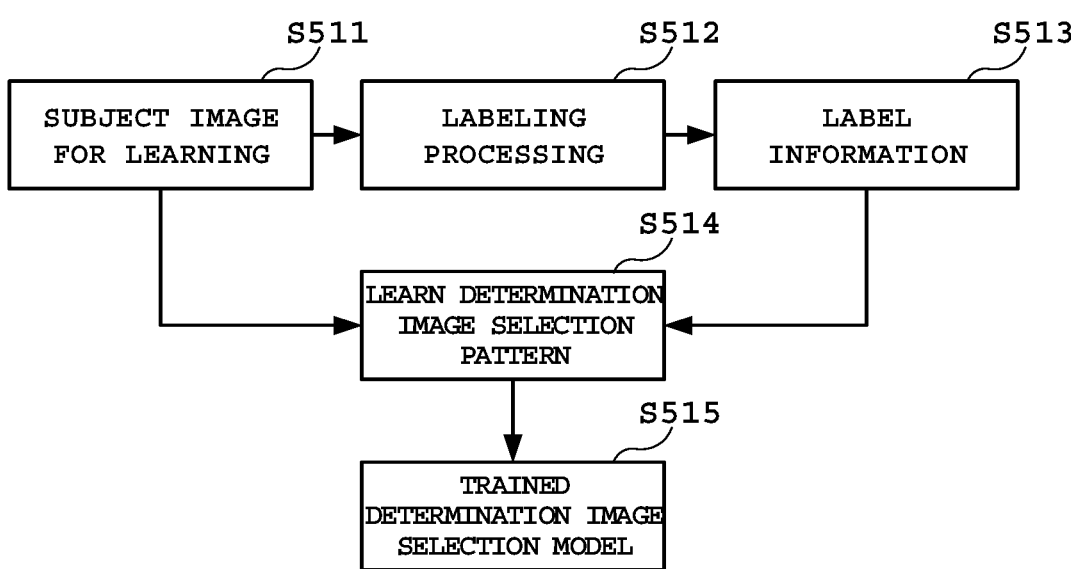
FIG. 13 is a diagram illustrating a processing flow related to generation of a trained model according to an embodiment of the present disclosure.

Here, FIG. 13 is a diagram illustrating a processing flow related to generation of a trained model according to an embodiment of the present disclosure. Specifically, FIG. 13 is a diagram illustrating a processing flow related to the generation of a trained determination image selection model used in S412 of FIG. 12. The processing flow may be executed by the processor 111 of the processing device 100 or may be executed by a processor of another processing device.

According to FIG. 13, the processor executes a step of acquiring a subject image of a subject including at least a part of the pharynx as a subject image for learning (S511). Then, the processor executes a processing step of assigning label information indicating whether an image can be used as a determination image to the acquired subject image for learning (S512). Then, the processor executes a step of storing the assigned label information in association with the subject image for learning (S513). Note that, in the labeling processing or the label information storage processing, whether the subject image for learning is a determination image may be determined in advance by a person, and the processor may store the determination image in association with the subject image for learning, or the processor may analyze whether the subject image for learning is a determination image by known image analysis processing and store the result in association with the subject image for learning. The label information is assigned based on viewpoints such as whether at least a part of the oral cavity as a subject is captured and whether the image quality is good in terms of camera shake, defocus, cloudiness, and the like.

When the subject image for learning and the label information associated with the subject image for learning are obtained, the processor executes a step of performing machine learning of a determination image selection pattern using the subject image for learning and the label information (S514). As an example, the machine learning is performed by providing a set of the subject image for learning and the label information to a neural network configured by combining neurons and repeating learning while adjusting parameters of each neuron so that the output of the neural network becomes the same as the label information. Then, a step of acquiring a trained determination image selection model (for example, a neural network and a parameter) is executed (S515). The acquired trained determination image selection model may be stored in the memory 112 of the processing device 100 or another processing device connected to the processing device 100 through a wired or wireless network.

Returning to FIG. 12 again, the processor 111 inputs the subject image read in S411 to the trained determination image selection model, thereby acquiring a candidate image as a candidate for the determination image as an output. As a result, it is possible to satisfactorily select an image in which at least a partial region of the oral cavity as a subject is captured or an image with good image quality in terms of camera shake, defocus, motion blur, exposure, and cloudiness of the subject. It is possible to stably select an image with good image quality regardless of the skill of the operator's imaging technique. Then, the processor 111 registers the acquired candidate image as a candidate for the determination image in the image management table.

Then, the processor 111 executes determination image selection processing based on the similarity from the selected candidate images (S413). Specifically, the processor 111 calculates the similarity between the candidate images by comparing the obtained candidate images with each other. Then, the processor 111 selects, as a determination image, a candidate image determined to have low similarity compared with other candidate images. Such similarity between the candidate images is calculated by a method using a local feature quantity in each candidate image (Bag-of-Keypoints method), a method using an earth mover's distance (EMD), a method using a support vector machine (SVM), a method using a Hamming distance, a method using cosine similarity, or the like.

In this manner, by calculating the similarity between the obtained candidate images and selecting a candidate image determined to have low similarity compared with other candidate images, subject images having different fields of view are selected as determination images. Therefore, it is possible to perform the determination processing based on more various kinds of information as compared with a case where subject images obtained in the same field of view are used as determination images. As a result, it is possible to further improve the determination accuracy. Specifically, even if a partial region of the pharynx is hidden by the uvula in a certain determination image, since a partial region of the pharynx hidden in another determination image having a different field of view is visible, it is possible to prevent important features, such as influenza follicles, from being overlooked.

Next, the processor 111 registers the candidate image selected based on the similarity in the image management table as a determination image (S414).

Here, the number of subject images, the number of candidate images, and the number of determination images may be one or more. However, as an example, it is preferable to select a candidate image group from a group of, for example, about 5 to 30 subject images and finally obtain a group of about five determination images. This is because selecting the determination image from a large number of subject images increases the possibility that a better determination image will be obtained. By using a plurality of determination image groups for determination processing to be described later, the determination accuracy can be further improved as compared with a case where only one determination image is used. As another example, every time the subject image is captured, the captured subject image may be transmitted to the processing device 100, and then the candidate image and the determination image may be selected, or the candidate image and the determination image may be selected in the imaging device 200, and the imaging may be ended when a predetermined number (for example, about 5) of determination images have been acquired. In this manner, it is possible to minimize the time related to the capturing of the subject image while maintaining the improvement in the determination accuracy as described above. In other words, it is possible to reduce discomfort to the user, such as vomiting reflex.

Figure 14:
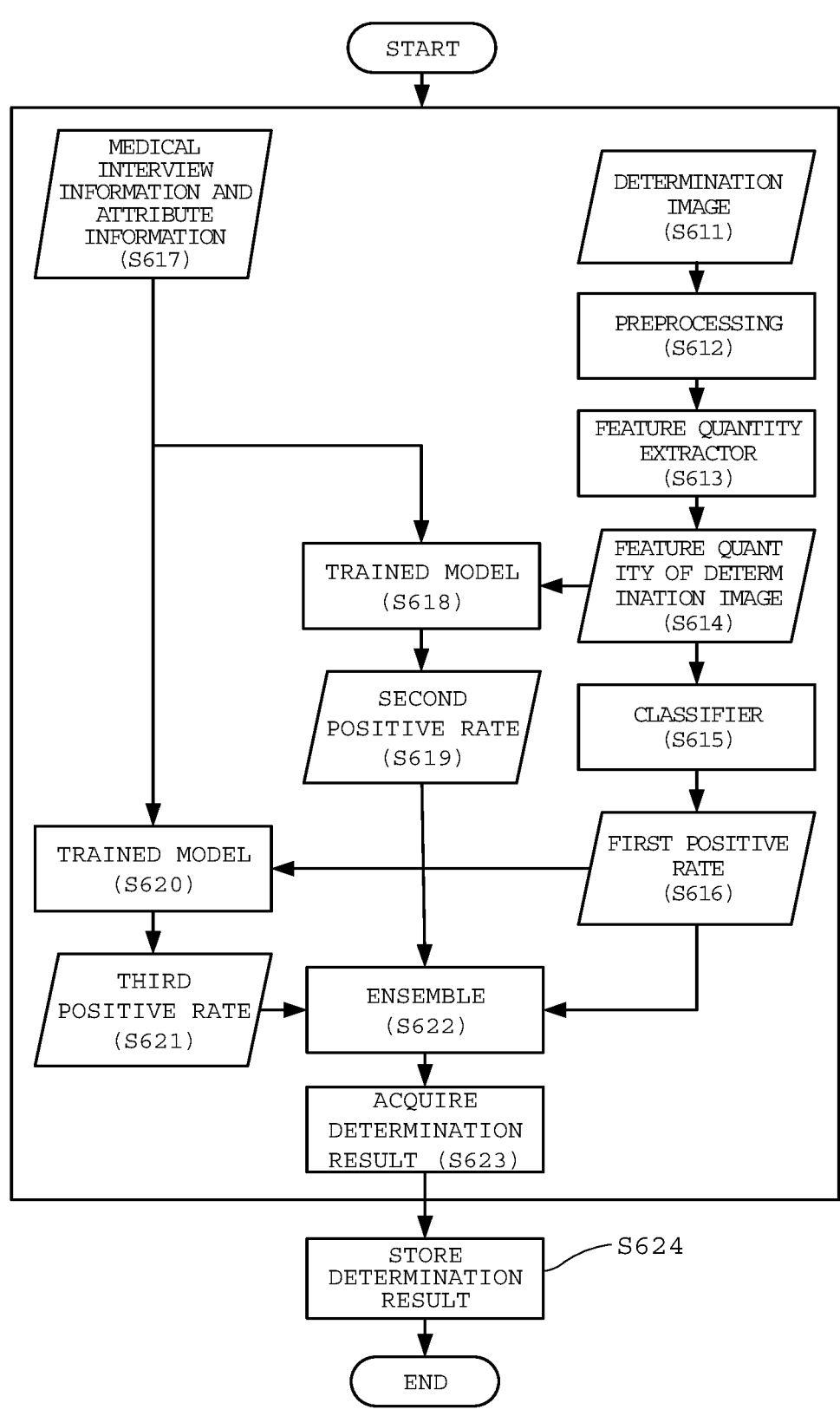
FIG. 14 is a diagram illustrating a processing flow executed in the processing device 100 according to an embodiment of the present disclosure.

FIG. 14 is a diagram illustrating a processing flow executed in the processing device 100 according to an embodiment of the present disclosure. Specifically, FIG. 14 is a diagram illustrating the details of processing for determining the possibility of contracting influenza, which is executed in S316 of FIG. 11. The processing flow is mainly performed by the processor 111 of the processing device 100 reading and executing a program stored in the memory 112.

According to FIG. 14, the processor 111 acquires the determination result by performing ensemble processing on the first positive rate, the second positive rate, and the third positive rate acquired by different methods.

First, processing for acquiring the first positive rate will be described. The processor 111 reads a determination image associated with the user ID information of the user as a determination target from the memory 112 (S611). Then, the processor 111 performs predetermined preprocessing on the read determination image. Such preprocessing is selected from filter processing using a bandpass filter including a high pass filter and a low pass filter, an averaging filter, a Gaussian filter, a Gabor filter, a Canny filter, a Sobel filter, a Laplacian filter, a median filter, and a bilateral filter, blood vessel extraction processing using a Hessian matrix and the like, segmentation processing of a specific region (for example, follicles) using machine learning, trimming processing for a segmented region, defogging processing, super-resolution processing, and combinations thereof according to purposes such as high definition, region extraction, noise removal, edge enhancement, image correction, and image conversion. In this manner, by executing the preprocessing, it is possible to improve the determination accuracy by extracting or emphasizing in advance a region of interest that is important in diagnosis for a disease, such as follicles in influenza.

Here, a case where the defogging processing, the super-resolution processing, and the segmentation processing are performed as such preprocessing will be specifically described below as an example. First, in the defogging processing, as an example, a trained defogging image model is used which is obtained by providing a set of a subject image for learning and a deteriorated image for learning, to which fogging is added by applying a fogging addition filter or the like to the subject image for learning, to a learning device and performing machine learning. The processor 111 inputs the read determination image as an input to the trained defogging image model stored in the memory 112, and acquires a determination image from which the fogging has been removed as an output. In the super-resolution processing, a trained super-resolution image model is used which is obtained by providing a set of a high-resolution image of a subject and a low-resolution image obtained by performing degradation processing, such as scale reduction processing or blurring processing, on the high-resolution image to a learning device as learning images and performing machine learning. The processor 111 inputs the determination image subjected to the defogging processing to the trained super-resolution image model stored in the memory 112, and acquires the determination image subjected to the super-resolution processing as an output. In the segmentation processing, a trained segmentation image model is used which is obtained by providing a set of a subject image for learning and position information of the label, which is obtained by assigning the label to the region of interest (for example, follicles) based on the operation input by the doctor to the subject image for learning, to the learning device and performing machine learning. The processor 111 inputs the determination image subjected to the super-resolution processing to the trained segmentation image model stored in the memory 112, and acquires a determination image in which the region of interest (for example, follicles) has been segmented. Then, the processor 112 stores the determination image preprocessed in this manner in the memory 112. Note that, here, the defogging processing, the super-resolution processing, and the segmentation processing are performed in this order, but may be performed in any order, or only at least one of the processes may be performed. Although all the processes are exemplified as processes using trained models, processing such as a defogging filter, scale enlargement processing, and sharpening processing may be used.

Then, the processor 111 provides the determination image after the preprocessing to a feature quantity extractor as an input (S613), and acquires the image feature quantity of the determination image as an output (S614). The processor 111 provides the acquired feature quantity of the determination image to a classifier as an input (S615), and acquires a first positive rate indicating the first possibility of contracting influenza as an output (S616). Note that, in the feature quantity extractor, a predetermined number of feature quantities such as the presence or absence of follicles and the presence or absence of redness in the determination image can be obtained as vectors. As an example, 1024-dimensional feature quantity vectors are extracted from the determination image, and these are stored as feature quantities of the determination image.

Figure 15:
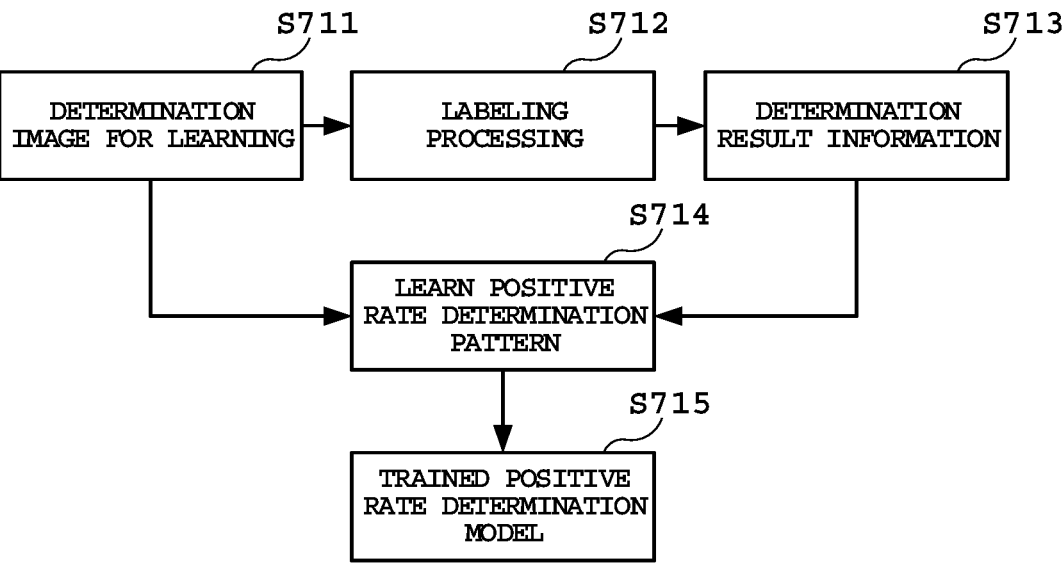
FIG. 15 is a diagram illustrating a processing flow related to generation of a trained model according to an embodiment of the present disclosure.

Here, FIG. 15 is a diagram illustrating a processing flow related to the generation of a trained model according to an embodiment of the present disclosure. Specifically, FIG. 15 is a diagram illustrating a processing flow related to the generation of a trained positive rate determination selection model including the feature quantity extractor in S613 and the classifier in S615 in FIG. 14. The processing flow may be executed by the processor 111 of the processing device 100 or may be executed by a processor of another processing device.

According to FIG. 15, the processor executes a step of acquiring, as a determination image for learning, an image obtained by performing preprocessing similar to that in S612 of FIG. 14 on an image of a subject including at least a part of a pharynx (S711). Then, the processor executes a processing step of assigning a correct label, which is assigned in advance based on the results of a rapid influenza test using immunochromatography, a PCR test, a virus isolation culture test, and the like, to the user who is the subject of the acquired determination image for learning (S712). Then, the processor executes a step of storing the assigned correct label information as determination result information in association with the determination image for learning (S713).

When the determination image for learning and the correct label information associated with the determination image for learning are obtained, the processor executes a step of performing machine learning of the positive rate determination pattern using these (S714). As an example, the machine learning is performed by providing a set of a determination image for learning and correct label information to a classifier including a feature quantity extractor, which includes a convolutional neural network, and a neural network and repeating learning while adjusting parameters of each neuron so that an output from the classifier becomes the same as the correct label information. Then, a step of acquiring a trained positive rate determination model is executed (S715). The acquired trained positive rate determination model may be stored in the memory 112 of the processing device 100 or another processing device connected to the processing device 100 through a wired or wireless network.

Returning to FIG. 14 again, the processor 111 inputs the determination image preprocessed in S612 to the trained positive rate determination model to acquire the feature quantity (S614) of the determination image and the first positive rate (S616) indicating the first possibility of contracting influenza as outputs, and stores the feature quantity and the first positive rate in the memory 112 in association with the user ID information.

Next, a process of acquiring the second positive rate will be described. The processor 111 reads, from the memory 112, at least one of the medical interview information and the attribute information associated with the user ID information of the user as a determination target (S617). The processor 111 also reads, from the memory 112, the feature quantity of the determination image calculated in S614 and stored in the memory 112 in association with the user ID information (S614). Then, the processor 111 provides at least one of the read medical interview information and attribute information and the feature quantity of the determination image as inputs to the trained positive rate determination model (S618), and acquires a second positive rate indicating the second possibility of contracting influenza as an output (S619).

Figure 16:
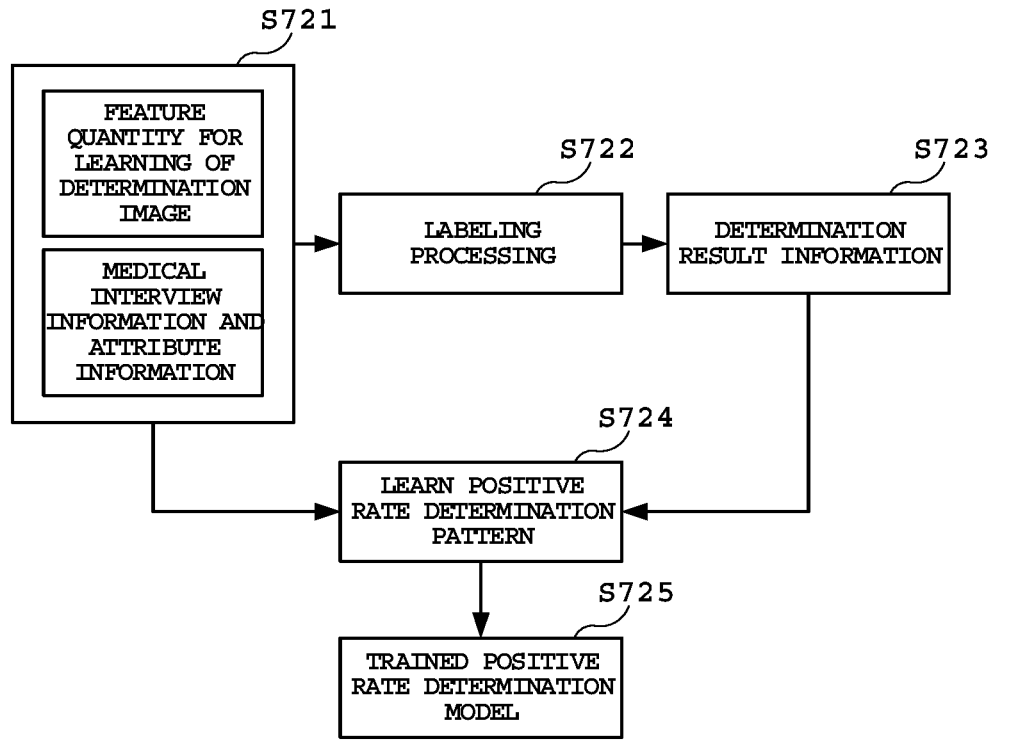
FIG. 16 is a diagram illustrating a processing flow related to generation of a trained model according to an embodiment of the present disclosure.

Here, FIG. 16 is a diagram illustrating a processing flow related to the generation of a trained model according to an embodiment of the present disclosure. Specifically, FIG. 16 is a diagram illustrating a processing flow related to the generation of the trained positive rate determination selection model in S618 of FIG. 14. The processing flow may be executed by the processor 111 of the processing device 100 or may be executed by a processor of another processing device.

According to FIG. 16, the processor executes a step of acquiring feature quantities for learning from the determination image obtained by performing the same preprocessing as that in S612 of FIG. 14 on the image of the subject including at least a part of the pharynx (S721). The processor executes a step of acquiring the medical interview information and the attribute information stored in advance in association with the user ID information of the user who is the subject of the determination image (S721). Then, the processor executes a processing step of assigning a correct label, which is assigned in advance based on the results of a rapid influenza test using immunochromatography, a PCR test, a virus isolation culture test, and the like, to the user who is the subject of the determination image (S722). Then, the processor executes a step of storing the assigned correct label information as determination result information in association with the feature quantity for learning of the determination image, the medical interview information, and the attribute information (S723).

When the feature quantity for learning of the determination image, the medical interview information and the attribute information, and the correct label information associated therewith are obtained, the processor executes a step of performing machine learning of the positive rate determination pattern using these (S724). As an example, the machine learning is performed by providing a set of these pieces of information to a neural network configured by combining neurons and repeating learning while adjusting parameters of each neuron so that the output of the neural network becomes the same as the correct label information. Then, a step of acquiring a trained positive rate determination model is executed (S725). The acquired trained positive rate determination model may be stored in the memory 112 of the processing device 100 or another processing device connected to the processing device 100 through a wired or wireless network.

Returning to FIG. 14 again, the processor 111 inputs the feature quantity of the determination image read in S614 and at least one of the medical interview information and the attribute information read in S617 to the trained positive rate determination model to acquire a second positive rate (S619) indicating the second possibility of contracting influenza as an output, and stores the second positive rate in the memory 112 in association with the user ID information.

Next, a process of acquiring the third positive rate will be described. The processor 111 reads, from the memory 112, at least one of the medical interview information and the attribute information associated with the user ID information of the user as a determination target (S617). The processor 111 also reads, from the memory 112, the first positive rate calculated in S616 and stored in the memory 112 in association with the user ID information. Then, the processor 111 provides at least one of the read medical interview information and attribute information and the first positive rate as inputs to the trained positive rate determination model (S620), and acquires a third positive rate indicating the third possibility of contracting influenza as an output (S621).

Figure 17:
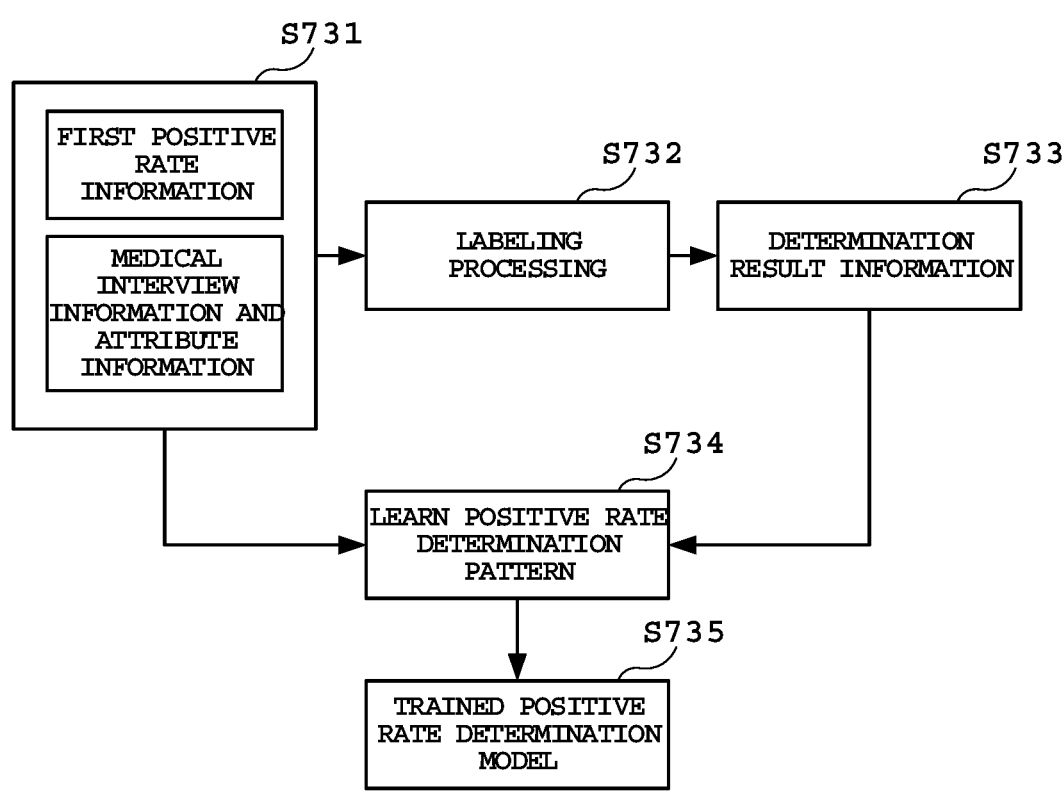
FIG. 17 is a diagram illustrating a processing flow related to generation of a trained model according to an embodiment of the present disclosure.

Here, FIG. 17 is a diagram illustrating a processing flow related to the generation of a trained model according to an embodiment of the present disclosure. Specifically, FIG. 17 is a diagram illustrating a processing flow related to the generation of the trained positive rate determination selection model in S620 of FIG. 14. The processing flow may be executed by the processor 111 of the processing device 100 or may be executed by a processor of another processing device.

According to FIG. 17, the processor executes a step of acquiring the first positive rate information obtained by inputting the determination image, which is obtained by performing the same preprocessing as in S612 of FIG. 14 on the image of the subject including at least a part of the pharynx, to the trained positive rate determination selection model including the feature quantity extractor (S613 in FIG. 14) and the classifier (S615 in FIG. 14) (S731). The processor executes a step of acquiring the medical interview information and the attribute information stored in advance in association with the user ID information of the user who is the subject of the determination image (S731). Then, the processor executes a processing step of assigning a correct label, which is assigned in advance based on the results of a rapid influenza test using immunochromatography, a PCR test, a virus isolation culture test, and the like, to the user who is the subject of the determination image (S732). Then, the processor executes a step of storing the assigned correct label information as determination result information in association with the first positive rate information, the medical interview information, and the attribute information (S733).

When the first positive rate information, the medical interview information and the attribute information, and the correct label information associated therewith are obtained, the processor executes a step of performing machine learning of the positive rate determination pattern using these (S734). As an example, the machine learning is performed by providing a set of these pieces of information to a neural network configured by combining neurons and repeating learning while adjusting parameters of each neuron so that the output of the neural network becomes the same as the correct label information. Then, a step of acquiring a trained positive rate determination model is executed (S735). The acquired trained positive rate determination model may be stored in the memory 112 of the processing device 100 or another processing device connected to the processing device 100 through a wired or wireless network.

Returning to FIG. 14 again, the processor 111 inputs the first positive rate information read in S616 and at least one of the medical interview information and the attribute information read in S617 to the trained positive rate determination model to acquire a third positive rate (S621) indicating the third possibility of contracting influenza as an output, and stores the third positive rate in the memory 112 in association with the user ID information.

When the first positive rate, the second positive rate, and the third positive rate are calculated in this manner, the processor 111 reads each positive rate from the memory 112 and performs ensemble processing (S622). As an example of the ensemble processing, the obtained first positive rate, second positive rate, and third positive rate are provided as inputs to a ridge regression model, and a result of ensemble of each positive rate is acquired as a determination result of the possibility of contracting influenza (S623).

Note that, the ridge regression model used in S622 is generated by machine learning by the processor 111 of the processing device 100 or a processor of another processing device. Specifically, the processor acquires each of the first positive rate, the second positive rate, and the third positive rate from the determination image for learning. The processor assigns a correct label, which is assigned in advance based on the results of a rapid influenza test using immunochromatography, a PCR test, a virus isolation culture test, and the like, to the user who is the subject of the determination image for learning. Then, the processor provides a set of each positive rate and a correct label associated therewith to the ridge regression model, and repeats learning while adjusting a parameter assigned to each positive rate so that the output becomes the same as correct label information of the ridge regression model. As a result, a ridge regression model used for the ensemble processing is obtained and stored in the memory 112 of the processing device 100 or another processing device connected to the processing device 100 through a wired or wireless network.

Although the case of using the ridge regression model has been described as an example of the ensemble processing, any method such as processing of acquiring the average value of positive rates, processing of acquiring a maximum value, processing of acquiring a minimum value, processing of performing weighted addition, and processing using other machine learning methods such as bagging, boosting, stacking, lasso regression, and linear regression may be used.

The processor 111 stores the determination result obtained in this manner in the user table of the memory 112 in association with the user ID information (S624). As described above, the processing flow ends.

Note that, in FIG. 14, ensemble processing is performed on the first positive rate, the second positive rate, and the third positive rate to finally obtain a determination result. However, the present invention is not limited thereto, and each of the positive rates may be used as it is as a final determination result, or ensemble processing based on any two positive rates may be performed to obtain a final determination result. Ensemble processing may be performed by further adding another positive rate obtained by another method, and a final determination result may be obtained.

As illustrated in FIG. 11, the obtained determination result is output through the output interface 114, but only the final determination result may be output, or each positive rate may be output together with the obtained determination result.

As described above, in the present embodiment, it is possible to provide a processing device, a processing program, a processing method, and a processing system suitable for processing an image obtained by imaging the inside of the oral cavity for use in diagnosis of the inside of the oral cavity.

8. Modification Examples

In the example of FIG. 14, the case of outputting the information indicating the possibility of contracting influenza using at least one of the medical interview information and the attribute information has been described. However, instead of or in addition to these pieces of information, external factor information related to influenza may be used to output the information indicating the possibility of contracting influenza. Examples of such external factor information include a determination result made for another user, a diagnosis result by a doctor, and influenza epidemic information in an area to which the user belongs. The processor 111 acquires such external factor information from another processing device or the like through the communication interface 115 and provides the external factor information as an input to the trained positive rate determination model, so that a positive rate considering the external factor information can be obtained.

In the example of FIG. 14, the case where the medical interview information and the attribute information are input in advance by the operator or the user or are received from the electronic medical record device or the like connected to the wired or wireless network has been described. However, these pieces of information may be obtained from a subject image captured instead of or in addition to these. Attribute information or medical interview information associated with a subject image for learning is provided as a correct label to the subject image for learning, and a set of these is machine-learned by the neural network to obtain a trained information estimation model. Then, the processor 111 provides a subject image to the trained information estimation model as an input, so that desired medical interview information and attribute information can be obtained. Examples of such medical interview information and attribute information include sex, age, a degree of redness of the pharynx, a degree of swelling of the tonsils, and presence or absence of white moss. As a result, it is possible to save time and effort for the operator to input the medical interview information and the attribute information.

Hereinafter, a case of obtaining the feature quantity of follicles in the pharynx will be described as a specific example of the medical interview information. As described above, follicles appearing in the pharynx region are a characteristic sign of influenza, and are also confirmed by visual inspection in diagnosis by a doctor. Therefore, processing for providing a label to a region of interest, such as follicles, is performed on the subject image for learning by an operation input by doctors. Then, the position information (shape information) of the label in the subject image for learning is acquired as position information for learning, and a set of the subject image for learning and the position information for learning labeled thereto is machine-learned by the neural network to obtain a trained region extraction model. Then, the processor 111 outputs the position information (shape information) of the region of interest (that is, follicle) by providing a subject image to the trained region extraction model as an input. Thereafter, the processor 111 stores the obtained follicle position information (shape information) as medical interview information.

A case of obtaining the heart rate as another specific example of the medical interview information will be described. First, the processor 111 receives a capturing time of a predetermined period as a subject image. Then, the processor 111 extracts each color component of RGB into each frame forming the received moving image, and obtains the brightness of a G (green) component. The processor 111 generates a brightness waveform of the G component in the moving image from the obtained brightness of the G component of each frame, and estimates the heart rate from the peak value. Note that, the method is a method using the fact that hemoglobin in blood absorbs green light, but it is needless to say that the heart rate may be estimated by other methods. Then, the processor 111 stores the heart rate estimated as described above as medical interview information.

In the example of FIG. 14, the case where the determination image read from the memory 112 is subjected to the preprocessing in S612 and then provided as an input to the feature quantity extractor has been described. However, the preprocessing is not necessarily required. For example, the processor 111 may read a determination image from the memory 112 and provide the read determination image to the feature quantity extractor as an input without preprocessing. Even when performing preprocessing, the processor 111 may provide both a determination image that has been subjected to the preprocessing and a determination image that has not been subjected to the preprocessing to the feature quantity extractor as inputs.

Also in the generation of each trained model illustrated in FIGS. 15 to 17, a determination image subjected to the same preprocessing as in S612 of FIG. 14 was used as learning data. However, as described above, in consideration of a case where the preprocessing is not performed in FIG. 14 or a case where both the determination image after the preprocessing and the determination image before the preprocessing are used as determination images, the determination image not subjected to the preprocessing may be used as learning data.

Each trained model described in FIGS. 13, 15 to 17, and the like is generated using a neural network or a convolutional neural network. However, the present invention is not limited thereto, and each trained model can be generated using machine learning, such as a nearest-neighbor method, a decision tree, a regression tree, and a random forest.

Figure 20:
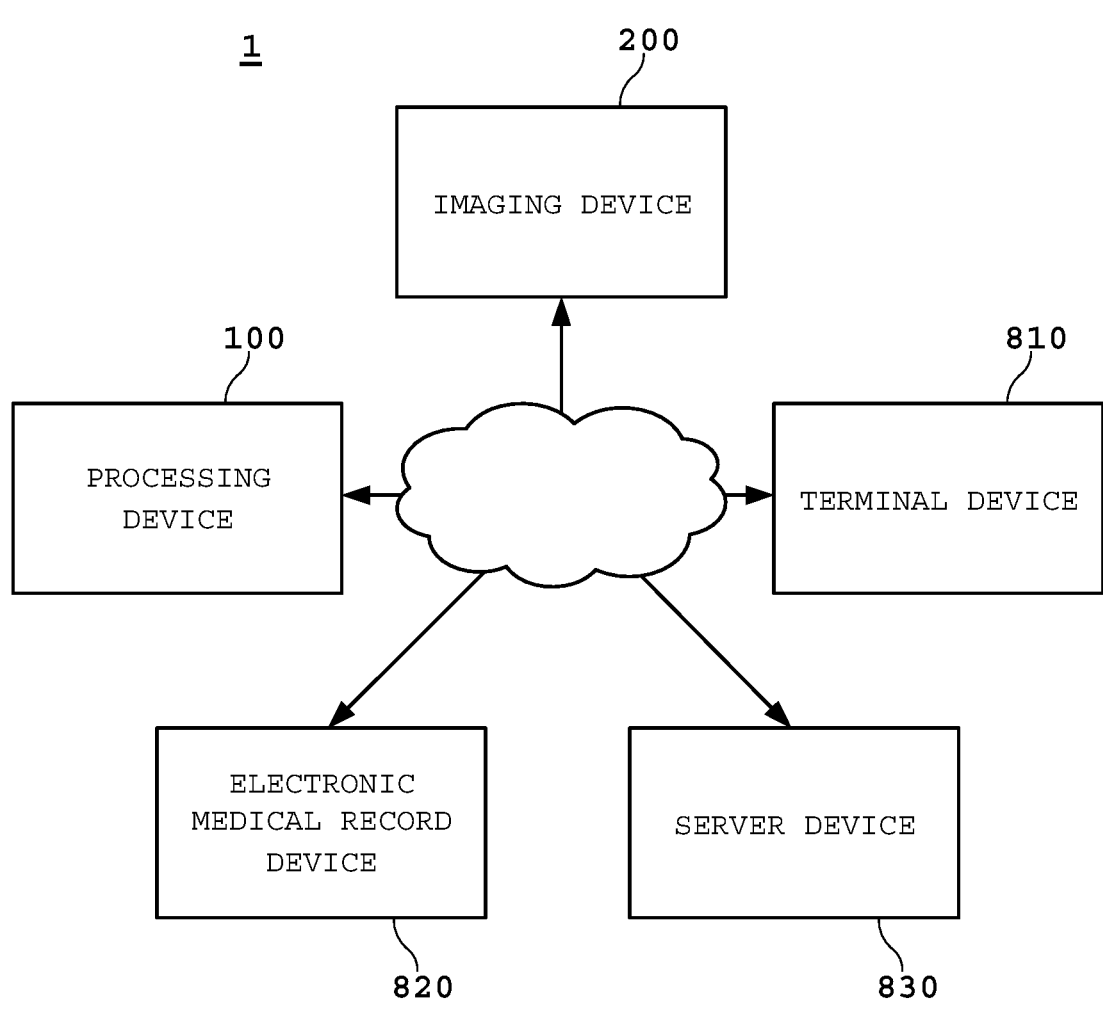
FIG. 20 is a schematic diagram of the processing system 1 according to an embodiment of the present disclosure.

In the example of FIG. 8, the case where the acquisition of attribute information or medical interview information, the selection of a determination image, determination processing, and the output of a determination result are performed in the processing device 100 and a subject image is captured by the imaging device 200 has been described. However, these various processes can be appropriately distributed and processed by the processing device 100, the imaging device 200, and the like. FIG. 20 is a schematic diagram of the processing system 1 according to an embodiment of the present disclosure. Specifically, FIG. 20 is a diagram illustrating a connection example of various devices that may form the processing system 1. According to FIG. 20, the processing system 1 includes the processing device 100, the imaging device 200, a terminal device 810 such as a smartphone, a tablet, or a laptop PC, an electronic medical record device 820, and a server device 830, which are connected to each other through a wired or wireless network. Note that, the devices illustrated in FIG. 20 are not necessarily provided, and may be appropriately provided according to a distribution example of processing exemplified below.

Instead of the example of FIG. 8, various processes can be distributed as follows in the processing system 1 illustrated in FIG. 20.

(1) All processes such as capturing of a subject image, acquisition of attribute information or medical interview information, selection of a determination image, determination processing, and output of a determination result are performed by the imaging device 200.

(2) Capturing of a subject image and output of a determination result are performed by the imaging device 200, and processing using machine learning, such as selection of a determination image and determination processing, is performed by the server device 830 (cloud server device).

(3) Input of medical interview information or attribute information is performed by the terminal device 810, selection of a determination image, determination processing, and output of a determination result are performed by the processing device 100, and capturing of a subject image is performed by the imaging device 200.

(4) Input of medical interview information or attribute information and capturing of a subject image are performed by the imaging device 200, and selection of a determination image, determination processing, and output of a determination result are performed by the processing device 100.

(5) Input of medical interview information or attribute information and output of a determination result are performed by the terminal device 810, selection of a determination image and determination processing are performed by the processing device 100, and capturing of a subject image is performed by the imaging device 200.

(6) Input of medical interview information or attribute information is performed by the electronic medical record device 820, selection of a determination image and determination processing are performed by the processing device 100, capturing of a subject image is performed by the imaging device 200, and output of a determination result is performed by the terminal device 810.

(7) Input of medical interview information or attribute information and output of a determination result are performed by the electronic medical record device 820, selection of a determination image and determination processing are performed by the processing device 100, and capturing of a subject image is performed by the imaging device 200.

(8) Input of medical interview information or attribute information and output of a determination result are performed by the terminal device 810, selection of a determination image and determination processing are performed by the server device 830, and capturing of a subject image is performed by the imaging device 200.

(9) Input of medical interview information or attribute information and output of a determination result are performed by the terminal device 810 and the electronic medical record device 820, selection of a determination image and determination processing are performed by the server device 830, and capturing of a subject image is performed by the imaging device 200.

(10) Input of medical interview information or attribute information and output of a determination result are performed by the electronic medical record device 820, selection of a determination image and determination processing are performed by the server device 830, and capturing of a subject image is performed by the imaging device 200.

An example of the distribution example of the above processing will be specifically described. In the terminal device 810 such as a smartphone held by a patient or the like, a tablet used in a medical institution or the like, and a laptop PC used by a doctor or the like, the processing according to S11 to S15 illustrated in FIG. 8 is executed. Thereafter, when the processing according to S21 to S24 is executed in the imaging device 200, a subject image is transmitted to the server device 830 through the terminal device 810 or directly. In the server device 830 that has received the subject image, the processing related to S31 and S32 is executed, and the determination result is output from the server device 830 to the terminal device 810. In the terminal device 810 that has received the output of the determination result, the determination result is stored in the memory and displayed on the display.

Note that, the above is merely an example of distribution of processing. In the present disclosure, the processing device 100 is referred to as a processing device. However, since various processes related to the determination processing and the like are simply executed, the processing device 100 is merely referred to as a processing device. For example, when the imaging device 200, the terminal device 810, the electronic medical record device 820, the server device 830, and the like execute various kinds of processing, these also function as processing devices and may be referred to as processing devices.

In the example of FIG. 3, a subject image is captured by using a substantially cylindrical imaging device 200 as the imaging device 200. However, the present invention is not limited thereto, and for example, it is also possible to use the terminal device 810 as an imaging device and capture a subject image using a camera provided in the terminal device 810. In such a case, the camera is not inserted to the vicinity of the pharynx in the oral cavity, but is disposed outside the incisors (outside the body) to image the inside of the oral cavity.

Note that, these modification examples are similar to the configurations, processes, and procedures in one embodiment described with reference to FIGS. 1 to 19, except for the points specifically described above. Therefore, a detailed description of these matters will be omitted. It is also possible to configure the system by appropriately combining or replacing each element described in each modification example or each embodiment.

The processing and procedures described in this specification can be implemented not only by those explicitly described in the embodiments but also by software, hardware, or a combination thereof. Specifically, the processing and procedures described in this specification are implemented by mounting logic corresponding to the processing on a medium such as an integrated circuit, a volatile memory, a nonvolatile memory, a magnetic disk, or an optical storage. The processing and procedures described in this specification can be implemented as a computer program and executed by various computers including a processing device or a server device.

Even if it is described that the processing and procedures described in this specification are executed by a single device, software, component, or module, such processing or procedures can be executed by a plurality of devices, a plurality of pieces of software, a plurality of components, and/or a plurality of modules. Even if it is described that various kinds of information described in this specification are stored in a single memory or storage unit, such information can be stored in a distributed manner in a plurality of memories provided in a single device or a plurality of memories arranged in a distributed manner in a plurality of devices. The software and hardware elements described in this specification can be implemented by integrating these into fewer components or decomposing these into more components.

The invention claimed is:

1. A processing device, comprising:

an interface configured to communicate with a camera, the camera being configured to capture a plurality of subject images of a subject, the plurality of subject images of the subject including a part of an oral cavity of a user;

a memory configured to store computer readable instructions, the plurality of subject images, which are obtained via the interface, a trained determination image selection model, and a trained determination model; and a processor configured to execute the computer readable instructions so as to:

perform a first machine leaning on a plurality of learning images having label information to learn a selection pattern for selecting a plurality of determination images from the plurality of subject images such that the trained determination image selection model is obtained, the plurality of learning images including a part of an oral cavity of a plurality of persons, the label information indicating whether an image, among the plurality of learning images, is used as one of the plurality of determination images, the plurality of determination images being used to determine whether the user contracts a predetermined disease;

perform a second machine learning on a plurality of learning determination images having disease positive label information, as the label information, to learn a positive rate determination pattern with respect to the plurality of determination images, the plurality of learning determination images including the part of the oral cavity of the plurality of persons;

obtain a plurality of candidate images by inputting the plurality of subject images into the trained determination image selection model, the plurality of candidate images having potential to become the plurality of determination images;

select the plurality of determination images from the plurality of candidate images based on a predetermined condition;

determine a possibility of contracting the predetermined disease of the user by inputting the plurality of determination images into the trained determination model to obtain a determination result; and output the determination result to a display to display the possibility of contracting the predetermined disease of the user.

2. The processing device according to claim 1, wherein the part of the oral cavity is pharynx.

3. The processing device according to claim 1, wherein the part of the oral cavity is tonsils.

4. The processing device according to claim 1, wherein the processor is further configured to obtain the plurality of determination images by selecting the images, from the plurality of candidate images, having a potential value that is lower than a threshold of a predetermined value, as the predetermined condition, when compared with other images among the plurality of candidate images.

5. The processing device according to claim 1, wherein the processor is further configured to:

calculate a predetermined feature quantity by inputting the plurality of determination images to a trained feature quantity extractor for extracting the predetermined feature quantity from the plurality of determination images; and determine the possibility of contracting the predetermined disease based on the predetermined feature quantity and the trained determination model.

6. The processing device according to claim 1, wherein the processor is further configured to:

acquire at least one of medical interview information and attribute information of the user; and determine the possibility of contracting the predetermined disease based on the trained determination model, the plurality of determination images, and at least one of the medical interview information and the attribute information.

7. The processing device according to claim 1, wherein the processor is further configured to:

acquire at least one of medical interview information and attribute information of the user;

determine a first possibility of contracting the predetermined disease based on the trained determination model and the plurality of determination images without using either the medical interview information or the attribute information to obtain a first sub-determination result;

determine a second possibility of contracting the predetermined disease based on the trained determination model, the plurality of determination images, and at least one of the medical interview information and the attribute information to obtain a second sub-determination result; and determine the possibility of contracting the predetermined disease based on the first sub-determination result and the second sub-determination result.

8. The processing device according to claim 6, wherein the attribute information is acquired from the plurality of subject images.

9. The processing device according to claim 1, wherein the processor is further configured to:

acquire external factor information related to the predetermined disease; and determine the possibility of contracting the predetermined disease based on the external factor information, the trained determination model, and the plurality of determination images.

10. A processing system, comprising:

the camera;

the display; and the processing device according to claim 1 connected to the camera through a wired or wireless network.

11. A computer program product embodying computer readable instructions stored on a non-transitory computer-readable storage medium for causing a computer to execute a process by a processor so as to perform the steps of:

storing a plurality of subject images, a trained determination image selection model, and a trained determination model into a memory, the plurality of subject images being obtained by capturing a subject by a camera, the plurality of subject images of the subject including a part of an oral cavity of a user;

performing a first machine leaning on a plurality of learning images having label information to learn a selection pattern for selecting a plurality of determination images from the plurality of subject images such that the trained determination image selection model is obtained, the plurality of learning images including a part of an oral cavity of a plurality of persons, the label information indicating whether an image, among the plurality of learning images, is used as one of the plurality of determination images, the plurality of determination images being used to determine whether the user contracts a predetermined disease;

performing a second machine learning on a plurality of learning determination images having disease positive label information, as the label information, to learn a positive rate determination pattern with respect to the plurality of determination images, the plurality of learning determination images including the part of the oral cavity of the plurality of persons;

obtaining a plurality of candidate images by inputting the plurality of subject images into the trained determination image selection model, the plurality of candidate images having potential to become the plurality of determination images;

selecting the plurality of determination images from the plurality of candidate images based on a predetermined condition;

determining a possibility of contracting the predetermined disease of the user by inputting the plurality of determination images into the trained determination model to obtain a determination result; and outputting the determination result to a display to display the possibility of contracting the predetermined disease of the user.

12. A processing method for causing a processor to execute a process, the processing method comprising executing on the processor the steps of:

storing a plurality of subject images, a trained determination image selection model, and a trained determination model into a memory, the plurality of subject images being obtained by capturing a subject by a camera, the plurality of subject images of the subject including a part of an oral cavity of a user;

performing a first machine leaning on a plurality of learning images having label information to learn a selection pattern for selecting a plurality of determination images from the plurality of subject images such that the trained determination image selection model is obtained, the plurality of learning images including a part of an oral cavity of a plurality of persons, the label information indicating whether an image, among the plurality of learning images, is used as one of the plurality of determination images, the plurality of determination images being used to determine whether the user contracts a predetermined disease;

performing a second machine learning on a plurality of learning determination images having disease positive label information, as the label information, to learn a positive rate determination pattern with respect to the plurality of determination images, the plurality of learning determination images including the part of the oral cavity of the plurality of persons;

obtaining a plurality of candidate images by inputting the plurality of subject images into the trained determination image selection model, the plurality of candidate images having potential to become the plurality of determination images;

selecting the plurality of determination images from the plurality of candidate images based on a predetermined condition;

determining a possibility of contracting the predetermined disease of the user by inputting the plurality of determination images into the trained determination model to obtain a determination result; and outputting the determination result to a display to display the possibility of contracting the predetermined disease of the user.

\* \* \* \* \*